(12) United States Patent
Christophers et al.

(10) Patent No.: US 6,893,843 B2
(45) Date of Patent: May 17, 2005

(54) NUCLEIC ACIDS

(75) Inventors: Enno Christophers, Kiel (DE); Oliver Wiedow, Jahnstr. 10, 2300 Kiel 1 (DE); Jens-Michael Schroder, Blumenthal (DE); Michael Derek Edge, Congleton (GB); David Pioli, Lymn (GB)

(73) Assignee: Oliver Wiedow, Kiel (DE)

( * ) Notice: Subject to any disclaimer, the term of this patent is extended or adjusted under 35 U.S.C. 154(b) by 45 days.

(21) Appl. No.: 09/833,799

(22) Filed: Apr. 13, 2001

(65) Prior Publication Data

US 2002/0187535 A1 Dec. 12, 2002

Related U.S. Application Data

(63) Continuation of application No. 08/427,170, filed on Apr. 24, 1995, now Pat. No. 6,245,739, which is a continuation of application No. 07/926,371, filed on Aug. 10, 1992, now Pat. No. 5,464,822, which is a continuation of application No. 07/536,096, filed on Jun. 8, 1990, now abandoned.

(51) Int. Cl.[7] .................. C12N 15/09; C12N 15/74; C07H 21/02

(52) U.S. Cl. .............. 435/69.2; 435/70.1; 435/71.1; 435/320.1; 435/468; 435/471; 435/476; 435/252.3; 435/254.11; 435/325; 536/23.1; 930/250

(58) Field of Search ................... 435/70.1, 71.1, 435/468, 471, 476, 183, 218, 320.1, 440, 455, 470, 325, 252.3, 254.11, 69.2; 530/300, 350; 536/23.1, 24.31, 24.33; 930/250

(56) References Cited

U.S. PATENT DOCUMENTS 5,370,991 A * 12/1994 O'Donnell
5,464,822 A   11/1995 Christophers et al.

OTHER PUBLICATIONS

New England BioLabs Catalog, 1986/87, pp. 60–62.*
Maniatis et al, Molecular Cloning A Laboratory Manual, Cold Spring Harbor Laboratory, 1982; pp. 249–251, 402–419.*
Seemuller et al, "The acid–stable proteinase inhibitor of human mucous secretions (HUS–I, antileukoprotease)", FEBS 199(1):3553 (1986).
Schalkwijk et al, "Skin–derived antileucoproteases (SKALPs): characterization of two new elastase inhibitors from psoriatic epidermis", British J. of Dermatology 122:631–641 (1990).

Wiedow et al, "Elafin: An Elastase–specific Inhibitor of Human Skin: Purification, Characterization, and Complete Amino Acid Sequence", J. of Biological Chemistry 265(25):14791, 14795 Sep. 1990.

Sallenave et al, "Isolation of elafin and elastase–specific inhibitor (ESI) from bronchial secretions evidence of sequence homology and immunological cross–reactivity", proposed publication.

Kramps et al, "Characterization of a Low Molecular Weight Anti–Elastase Isolated from Human Bronchial Secretion", Experimental Lung Research 9:151–165 (1985).

Schalkwyk et al, Abstracts for the 18th Annual Meeting of the European Society of Dermatologic Research, Psoriasis (Abstracts 1–12) No. 2.

Wiedow et al, "Elafin purification and characterization of a new elastase–specific protease inhibitor derived from psoriatic scales", Dept. of Dermatology, Univ. of Kiel, FRG, ADF–Abstracts, p. 559, 1990.

Hochstrasser et al, "An Elastase Specific Inhibitor from Bronchial Mucus", Hoppe–Seyler's Z Physiol. Chem. Bd. 362:1369–1375 (1981).

Weinbaum et al, "Protease Inhibitor Therapy in Emphysema: a promising theory with Problems", Current Awareness TIPS 8:6–9 (1987).

Jackman, Applications of Nuclear Magnetic Resonance Spectroscopy in Organic Chemistry.

* cited by examiner

Primary Examiner—Patricia A. Duffy
(74) Attorney, Agent, or Firm—Nixon & Vanderhye P.C.

(57) ABSTRACT

Polypeptides, in particular the polypeptide of formula I:

```
Ala-Gln-Glu-Pro-Val-Lys-Gly-Pro-Val-Ser-Thr-Lys-
Pro-Gly-Ser-Cys-Pro-Ile-Ile-Leu-Ile-Arg-Cys-Ala-
Met-Leu-Asn-Pro-Pro-Asn-Arg-Cys-Leu-Lys-Asp-Thr-
Asp-Cys-Pro-Gly-Ile-Lys-Lys-Cys-Cys-Glu-Gly-Ser-
Cys-Gly-Met-Ala-Cys-Phe-Val-Pro-Gln
``` and analogues thereof which possess inhibitory activity against human leukocyte elastase. The polypeptides may be obtained by expression using plasmidic expression systems in hosts such as *E. Coli* and yeast, the polypeptide of formula I being also obtainable from psoriatic plaques.

7 Claims, 17 Drawing Sheets

Fig.6.
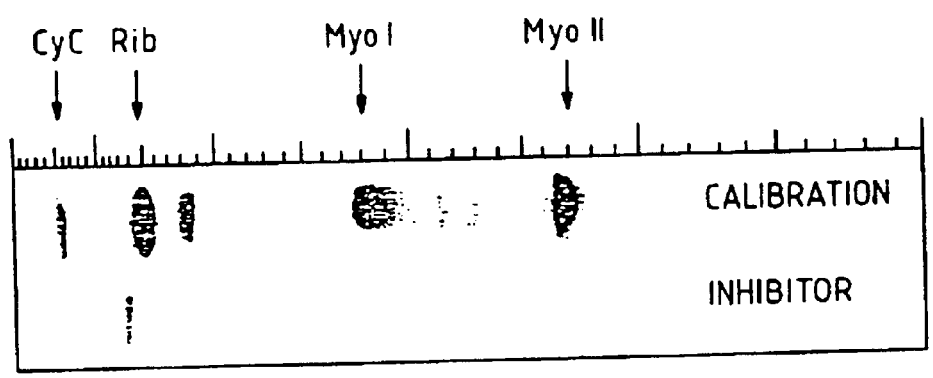
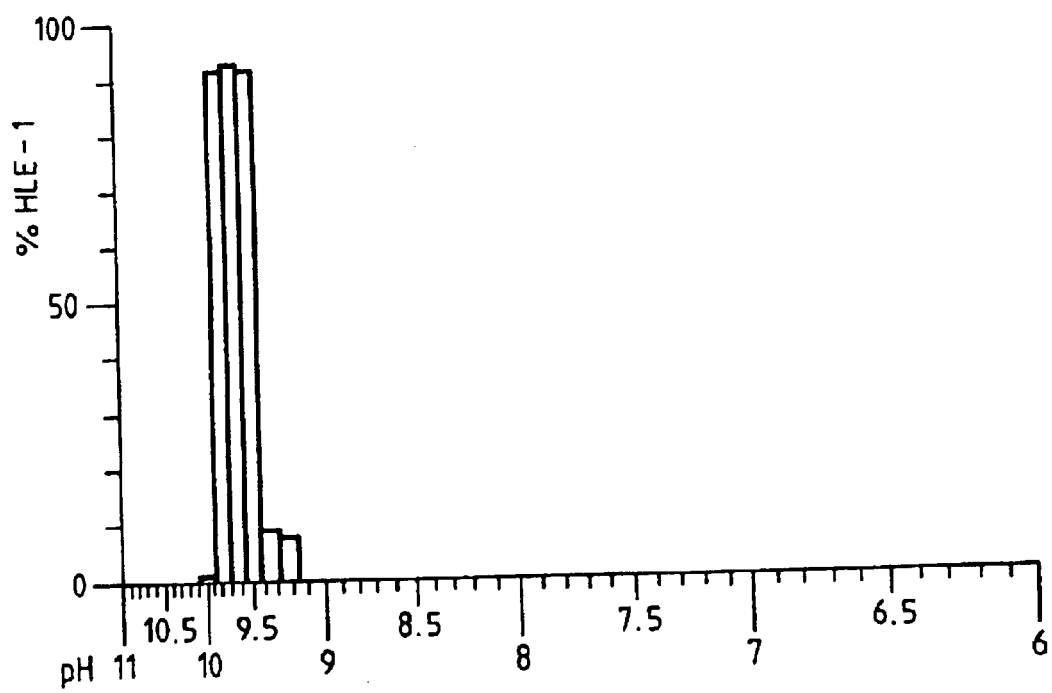

Fig. 13.

```
                              AlaGlnGluProValLysGlyProValSerThr
1    ┌──▶    ELI1
     │AATTCGAGCTCGGTACCATACCTGCATATGCTCAAGAACCAGTTAAAGGTCCTGTGTCTACT
          GCTCGAGCCATGGTATGGACGTATACGAGTTCTTGGTCAATTTCCAGGACACAGATGA

LysProGlySerCysProIleIleLeuIleArgCysAlaMetLeuAsnProProAsnArg
63   ┌──▶    ELI3
     │
     AAGCCAGGTTCTTGTCCTATTATCTTGATTCGTTGCGCTATGTTAAACCCACCTAACCGT
     TTCGGTCCAAGAACAGGATAATAGAACTAAGCAACGCGATACAATTTGGGTGGATTGGCA
     ELI2 ◀──┘

CysLeuLysAspThrAspCysProGlyIleLysLysCysCysGluGlySerCysGlyMet
123           ┌──▶    ELI5
     TGTTTGAAGGACACTGATTGTCCAGGTATCAAAAAGTGCTGTGAAGGTTCCTGCGGTATG
     ACAAACTTCCTGTGACTAACAGGTCCATAGTTTTTCACGACACTTCCAAGGACGCCATAC
              ELI4 ◀──┘

AlaCysPheValProGlnEndEnd
183  GCTTGTTTCGTTCCACAATAATAG

CGAACAAAGCAAGGTGTTATTATCCTAG    210
              ELI6 ◀──
```

Fig. 14.

```
Ala Gln Glu Pro Val Lys Gly Pro Val Ser Thr Lys Pro Gly Ser Cys
GCG CAA GAG CCA GTC AAA GGT CCA GTC TCC ACT AAG CCT GGC TCC TGC
5' DNA
Sequence Pro Ile Ile Leu Ile Arg Cys Ala Met Leu Asn Pro Pro Asn Arg Cys
CCC ATT ATC TTG ATC CGG TGC GCC ATG TTG AAT CCC CCT AAC CGC TGC Leu Lys Asp Thr Asp Cys Pro Gly Ile Lys Lys Cys Cys Glu Gly Ser

TTG AAA GAT ACT GAC TGC CCA GGA ATZ AAG AAP TGC TGT GAA GGC TCT

Cys Gly Met Ala Cys Phe Val Pro Gln
TGC GGG ATG GCC TGT TTC GTT CCC CAG

Z = T, C or A
P = A or G
```

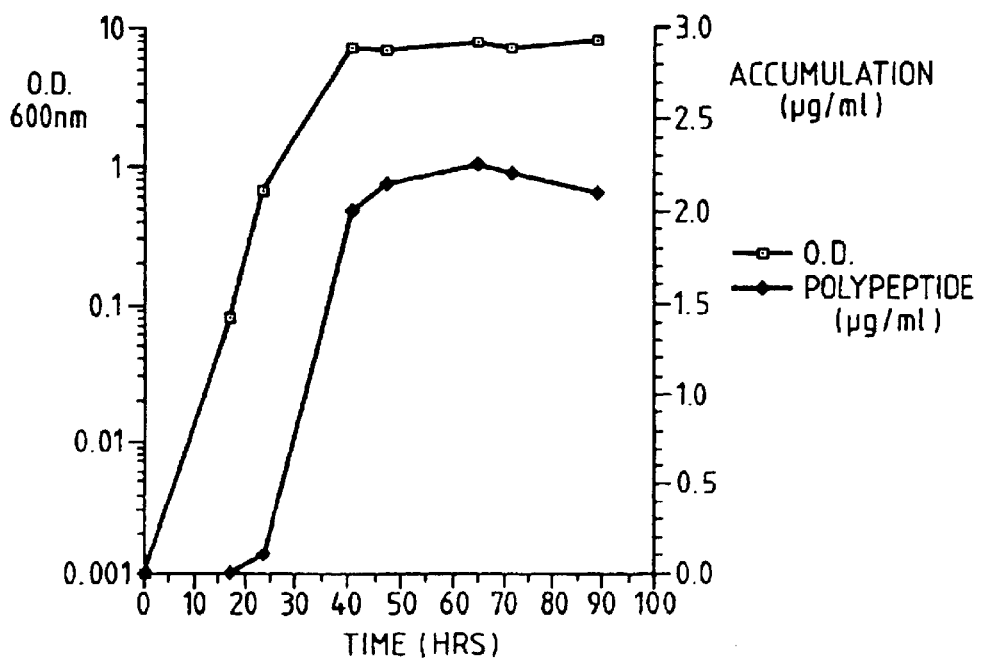

```
Ala Gln Glu Pro Val Lys Gly Pro Val Ser Thr Lys Pro Gly Ser Cys
GCG CAA GAG CCA GTC AAA GGT CCA GTC TCC ACT AAG CCT GGC TCC TGC
5' DNA
Sequence Pro Ile Ile Leu Ile Arg Cys Ala Met Leu Asn Pro Pro Asn Arg Cys
CCC ATT ATC TTG ATC CGG TGC GCC ATG TTG AAT CCC CCT AAC CGC TGC Leu Lys Asp Thr Asp Cys Pro Gly Ile Lys Lys Cys Cys Glu Gly Ser

TTG AAA GAT ACT GAC TGC CCA GGA ATZ AAG AAP TGC TGT GAA GGC TCT

Cys Gly Met Ala Cys Phe Val Pro Gln
TGC GGG ATG GCC TGT TTC GTT CCC CAG  TAG GAGGGAGCCGGTCCTTGCTGCACCTGT

GCCGTCCCCAGAGCTACAGGCCCCATCTGGTCCTAAGTCCCTGCTGCCCTTCCCCTTCCCACACTGTCCA
TTCTTCCTCCCATTCAGGATGCCCACGGCTGGAGCTGCCTCTCTCATCCACTTTCCAATAAAGAGTTCCG
GAATTC                                                      Poly A  3'
                                                             signal
```

```
              10                        30                        50
               .                         .                         .
       .       .       .       .       .       .       .       .
GGAATTCCGGTTCCTCATCGCTGGGACGCTGGTTCTAGAGGCAGCTGTCACGGGAGTTCC
EcoRI                           XbaI
  F  L  I  A  G  T  L  V  L  E  A  A  V  T  G  V  P
|--------IN-FRAME UPSTREAM PROTEIN SEQUENCE-------
     70                        90                       110
      .                         .                         .
     .       .       .       .       .       .       .       .
TGTTAAAGGTCAAGACACTGTCAAAGGCCGTGTTCCATTCAATGGACAAGATCCCGTTAA
  V  K  G  Q  D  T  V  K  G  R  V  P  F  N  G  Q  D  P  V  K
    130                       150                       170
      .                         .                         .
      .       .       .       .       .       .       .       .
AGGACAAGTTTCAGTTAAAGGTCAAGATAAAGTCAAAGCGCAAGAGCCAGTCAAAGGTCC
  G  Q  V  S  V  K  G  Q  D  K  V  K
                                     AlaGlnGluProValLysGlyPr
                                    |--ELASTASE INHIBITOR--
```

Fig. 16 (cont.)

```
            190                 210                 230
             .         .         .         .         .         .
AGTCTCCACTAAGCCTGGCTCCTGCCCCATTATCTTGATCCGGTGCGCCATGTTGAATCC
oValSerThrLysProGlySerCysProIleIleLeuIleArgCysAlaMetLeuAsnPr 250                 270                 290
             .         .         .         .         .         .
CCCTAACCGCTGCTTGAAAGATACTGACTGCCCAGGAATCAAGAAGTGCTGTGAAGGCTC
oProAsnArgCysLeuLysAspThrAspCysProGlyIleLysLysCysCysGluGlySe
            310                 330                 350
             .         .         .         .         .         .
TTGCGGGATGGCCTGTTTCGTTCCCCAGTGAGAGGGAGCCGGTCCTTGCTGCACCTGTGC
rCysGlyMetAlaCysPheValProGlnEnd
            370                 390                 410
             .         .         .         .         .         .
CGTCCCCAGAGCTACAGGCCCCATCTGGTCCTAAGTCCCTGCTGCCCTTCCCCTTCCCAC 430                 450                 470
             .         .         .         .         .         .
ACTGTCCATTCTTCCTCCCATTCAGGATGCCCACGGCTGGAGCTGCCTCTCTCATCCACT

490
             .         .
TTCCAATAAAGAGTTCCGGAATTC
     Poly A         EcoRI
     signal
```

```
        EcoRI  SmaI BamHI   SalI            PstI
          |     |    |       |               |
pUEX2   GAA TTC CCG GGG ATC CGT CGA CCT GCA GCC AAG CTT GCT GAT TGA
        Glu Phe Pro Gly Ile Arg Arg Pro Ala Ala Lys Leu Ala Asp ***
```

NUCLEIC ACIDS

This is a continuation of application Ser. No. 08/427,170, filed Apr. 24, 1995, now U.S. Pat. No. 6,245,739; which is a continuation of application Ser. No. 07/926,371, filed Aug. 10, 1992, now U.S. Pat. No. 5,464,822; which is a continuation of application Ser. No. 07/536,096, filed Jun. 8, 1990, now abandoned, the entire content of which is hereby incorporated by reference in this application.

This invention relates to polypeptides which possess inhibitory activity against human elastase, processes for their preparation and pharmaceutical compositions containing them as well as to the genetic modification of hosts to express the said polypeptides, the hosts thereby obtained, the genetic material employed in the modification and vectors therefor.

Human leukocyte elastase (HLE) is a proteolytic enzyme which is present in the azurophil granules of human polymorphonuclear leukocytes. Under normal circumstances these granules fuse with phagosomes containing foreign material, such as bacteria, and the particles are metabolised by a combination of HLE and other lysomal enzymes. However, under certain pathological conditions the polymorphonuclear leukocytes become attached to host protein, such as elastin and collagen, and the contents of the granules, including HLE, may be released directly onto the tissue. The resulting degradative activity of HLE on the host tissue is believed to lead to tissue damage which may play a role in diseases such as emphysema (2), adult respiratory distress syndrome (1), psoriasis (3) and bullous dermatoses (4).

The potent proteolytic activity of HLE is known to be balanced to a certain extent by the antiproteolytic activity of inhibitors such as Alpha$_1$-antitrypsin and Alpha$_2$-macroglobulin. These inhibitors have been detected in serum as well as various tissues including epidermis (5,10). In addition, a low molecular weight inhibitor of human leukocyte proteases has been shown to be present in seminal fluid (11), cervical mucus (12), bronchial secretion (13) and parotid secretion (14) as well as in human serum (6). The inhibitor from all these sources was shown to be identical with antileukoprotease and its metabolites by immunoreactivity (6,15) or amino acid sequence analysis (16,17), and to also be a potent inhibitor of trypsin. Low molecular weight inhibitors have also been detected in bronchial mucus by Hochstrasser et al (21), and in psoriatic skin (22). The literature also reports other inhibitors of elastase (18,19) which also inhibit trypsin. In addition, elastase inhibitors have been detected in the submandibular glands of dogs, lions and cats (20).

According to one first feature of the present invention there is provided a polypeptide having all or part of the primary structure of formula I and fragments thereof, Ala-Gln-Glu-Pro-Val-Lys-Gly-Pro-Val-Ser-Thr-Lys-Pro-Gly-Ser-Cys-Pro-Ile-Ile-Leu-Ile-Arg-Cys-Ala-Met-Leu-Asn-Pro-Pro-Asn-Arg-Cys-Leu-Lys-Asp-Thr-Asp-Cys-Pro-Gly-Ile-Lys-Lys-Cys-Cys-Glu-Gly-Ser-Cys-Gly-Met-Ala-Cys-Phe-Val-Pro-Gln. (Formula I) which polypeptide or fragments possess inhibitory activity against human leukocyte elastase, and compounds capable of being modified in vivo or in vitro to said polypeptide or fragments.

According to the present invention there is also provided a polypeptide which comprises all or part of the following primary structure and fragments thereof:
Lys-Gly-Pro-Val-Ser-Thr-Lys-Pro-Gly-Ser-Cys-Pro-Ile-Ile-Leu-Ile-Arg-Cys-Ala-Met-Leu-Asn-Pro-Pro-Asn-
which polypeptide or fragments possess inhibitory activity against human leukocyte elastase, and compounds capable of being modified in vivo or in vitro to said polypeptide or fragments.

Conveniently, the polypeptide or fragments have the structure:
Lys-Gly-Pro-Val-Ser-Thr-Lys-Pro-Gly-Ser-Cys-Pro-Ile-Ile-Leu-Ile-Arg-Cys-Ala-Met-Leu-Asn-Pro-Pro-Asn-X; wherein X comprises one or more amino acid residues and is preferably Arg-Cys-Leu-Lys-Asp-Thr-Asp-Cys-Pro-Gly-Ile-Lys-Lys-Cys-Cys-Glu-Gly-Ser-Cys-Gly-Met-Ala-Cys-Phe-Val-Pro-Gln.

The polypeptide may be preceded by one or more amino acid residues, for example Ala-Gln-Glu-Pro-Val-; or Y-Ala-Gln-Glu-Pro-Val- wherein Y comprises one or more amino acids which may be, for example:
Asn-Gly-Gln-Asp-Pro-Val-Lys-Gly-Gln-Val-Ser-Val-Lys-Gly-Gln-Asp-Lys-Val-Lys-;
Gly/Ala-Gln/Val-Asp-Lys-Val-Lys-;
Asp-Lys-Val-Lys-; or
Gly/Val-Lys- Most preferably the polypeptide has the structure of formula I Conveniently, the polypeptide or fragments of the present invention possess inhibitory activity which is specific for serine proteases, in that they possess inhibitory activity against proteases such as human leukocyte elastase and porcine pancreatic elastase; but do not possess any significant inhibitory activity against trypsin. Preferred polypeptides or fragments of the invention do not possess any significant inhibitory activity against human cathepsin G, Alpha-chymotrypsin and plasmin.

Polypeptides, or fragments thereof, of the present invention may have an isoelectronic point at about pH 9.7 (as determined by isoelectronic focussing).

Although they may be prepared by genetic engineering techniques the preferred polypeptides of the present invention may also be obtained from psoriatic scales of human skin.

According to the present invention there is also provided a polypeptide which possesses inhibitory activity against human leukocyte elastase, said polypeptide being obtainable from psoriatic scales of human skin and possessing one or more of the following characteristics:
a) a molecular weight of about 9 kD (as determined by SDS-PAGE);
b) an isoelectronic point at about pH 9.7 (as determined by isoelectronic focusing);
c) inhibitory activity against porcine pancreatic elastase in addition to human leukocyte elastase;
d) no significant activity against trypsin, human cathepsin G, Alpha-chymotrypsin and plasmin; or a fragment thereof possessing inhibitory activity against human leukocyte elastase.

Polypeptides obtainable from human skin include those obtainable directly by means of isolation and purification procedures and also fragments of such polypeptides.

Preferred polypeptides of the present invention contain one of the following amino acid sequences:
a) -Ala-Gln-Glu-Pro-Val-Lys-Gly-Pro-
and most preferably a N-terminal sequence comprising the above sequence preceded by X,
where X represents an amino acid sequence which may contain 19 amino acids, which sequence is conveniently
Asn-Gly-Gln-Asp-Pro-Val-Lys-Gly-Gln-Val-Ser-Val-Lys-Gly-Gln-Asp-Lys-Val-Lys-
b) -Ala-Gln-Glu-Pro-Val-Lys-Gly-Pro-Val-Ser-Thr-Lys-Pro-Gly-Ser-Cys-Pro-Ile-Ile-Leu-
and most preferably a N-terminal sequence comprising the above sequence preceded by X, where X represents an amino-acid sequence which may contain six amino acids, which sequence is conveniently
Gly/Ala-Gln/Val-Asp-Lys-Val-Lysc) -Ala-Gln-Glu-Pro-Val-Lys-Gly-Pro-Val-Ser-Thr-Lys-Pro-Gly-Ser-Cys
and most preferably a N-terminal sequence which comprises the above sequence preceded by X,
where X represents an amino acid sequence which may contain four amino acids, which sequence is conveniently
Asp-Lys-Val-Lysd) Ala-Gln-Glu-Pro-Val-Lys-Gly-Pro-Val-Ser-Thr-Lys-Pro-Gly-Ser-Cys-Pro-Ile-Ile-Leu-Ile-Arg-Cys-Ala-Met-Leu-Asn-Pro-Pro-Asn-Arg-Cys-Leu-Lys-Asp-Thr-
and most preferably a N-terminal sequence which comprises the above sequence preceded by X, where X represents an amino acid sequence which may contain two amino acid residues which are conveniently
Gly/Val-Lys e) Lys-Gly-Pro-Val-Ser-Thr-Lys-Pro-Gly-Ser-Cys-Pro-Ile-Ile-Leu-Ile-Arg-Cys-Ala-Met-Leu-Asn-Pro-Pro-Asn-
and most preferably a polypeptide having an N-terminal sequence which comprises the above sequence.

Particularly preferred polypeptides are as defined in the first aspect of the present invention, especially the polypeptide of formula I.

The polypeptide of formula I also possesses inhibitory activity against protinase 3.

The polypeptides and fragments thereof of the present invention are obtainable in a biologically pure and homogenous form. The present invention also provides a polypeptide as herein defined unaccompanied by associated native glycosylation.

In addition to polypeptides as hereinbefore defined, the present invention also embraces other products which possess inhibitory activity against human leukocyte elastase, such as polypeptide analogues. Therefore, according to the present invention there is also provided polypeptide analogues of the polypeptides as hereinbefore defined which analogues possess inhibitory activity against human leukocyte elastase.

These polypeptide analogues include polypeptides which differ from that hereinbefore defined in terms of the identity or location of one or more amino acid residues. For example, such analogues may contain substitutions, or terminal or intermediate additions or deletions of such residues. Such analogues would share an inibitory activity against human leukocyte elastase and may if desired share one or more additional activities of the polypeptide of formula I such as inhibitory activity against porcine pancreatic elastase. As examples, projected products of the invention include those which are more stable to hydrolysis (and, therefore, may have more pronounced or longer lasting effects than naturally-occurring); or which have one or more cysteine residues deleted or replaced by, e.g., alanine or serine residues and are potentially more easily isolated in active form from microbial systems.

The polypeptides, fragments and polypeptide analogues of the present invention may be obtained in a biologically pure and homogenous form.

The polypeptides of the present invention may conveniently be prepared by genetic engineering techniques. Analogues of the present invention may be prepared by expression of genes coding for such analogues. Such genes may readily be obtained by modifications of cDNA and genomic genes by well-known site directed mutagenesis techniques.

Thus, according to a further feature of the present invention there is provided a polypeptide (as herein defined), or an analogue thereof, as produced by recombinant DNA technology.

According to a further feature of the present invention there is provided a process for producing a polypeptide as hereinbefore defined, said process comprising culturing a host cell transformed with a replicable plasmidic expression vehicle comprising genetic material coding for the said polypeptide so that said polypeptide is expressed, and recovering the polypeptide so expressed.

The term replicable plasmidic expression vehicle as used herein is used in its broadest sense and includes, for example plasmids which are able to replicate in a cell as an extra-chromosomal element and those which are able to replicate by integration into the genetic material of the host cell.

The above-mentioned process may be effected by the use of any appropriate host cell such as *E. coli*, yeast or mammalian cells. Depending upon the host employed polypeptides of the invention may be glycosylated with mammalian or other eucaryotic carbohydrates or they may be non-glycosylated.

It will be appreciated that where the desired metabolite is not passed out of the host cell at a commercially useful rate, the host may be cultured and harvested as the intact cell and the desired polypeptide recovered by subsequently extracting the cells, for example after separation from the medium containing nutrients necessary for growth of the host cell. Where the metabolite is passed out of the host cell into the surrounding culture solution, then the polypeptide may be recovered by extraction in the normal way.

According to a further feature of the present invention there is therefore provided a transformant host capable of expressing a polypeptide as hereinbefore defined, the host comprising a replicable plasmidic expression vehicle, said vehicle comprising genetic material coding for the said polypeptide.

According to a further feature of the present invention there is provided a process for the preparation of a transformant host as hereinbefore defined, said process comprising transforming a host by the insertion therein of a replicable plasmidic expression vehicle which vehicle comprises genetic material coding for a polypeptide as hereinbefore defined.

Suitable methods for the introduction of foreign genetic material into host are generally known from the literature. Such methods include formation of a replicable expression vehicle comprising a vector and the foreign genetic material, and introduction of the vehicle into the host. Introduction of the vehicle into the host may be facilitated by subjecting the host to an appropriate treatment, for example in the case of *E. Coli.* by treatment with calcium chloride solution.

According to a further feature of the present invention there is provided a replicable plasmidic expression vehicle capable, in a transformant host, of expressing a polypeptide as hereinbefore defined.

Thus, there is also provided a process for the preparation of such a replicable plasmidic expression vehicle, said process comprising inserting a gene coding for a polypeptide as hereinbefore defined into a vector at an appropriate insertion site so that a replicable plasmidic expression vehicle is obtained which is capable of directing the synthesis of a polypeptide as hereinbefore defined.

According to a further feature of the present invention there is provided a DNA sequence that codes for a polypeptide as hereinbefore defined.

DNA sequences of the invention include sequences useful in securing expression in procaryotic or eucaryotic host cells of a polypeptide as hereinbefore defined. DNA sequences of the invention are specifically seen to comprise:

a) a DNA sequence set forth in FIG. 13 and fragments thereof, and in particular the fragment which codes for the polypeptide of formula I, or its complementary strand;
b) a DNA sequence which hydridises to a DNA sequence set forth in FIG. 13 or to a fragment thereof; and
c) a DNA sequence which, but for the degeneracy of the genetic code, would hydridise to a DNA sequence set forth in FIG. 13 or to a fragment thereof, and in particular to the fragment which codes for the polypeptide of formula I.

Specifically comprehended in part b) are genomic DNA sequences encoding allelic variant forms of the polypeptide of formula I. Specifically comprehended by part c) are manufactured DNA sequences. Manufactured sequences may readily be manufactured according to the methods of Alton et al. PCT published application WO83/04053; and Edge et al, Nature Vol 292, 756–762, 1981.

The fragments of sequences illustrated in FIG. 13 referred to above include those generated by sequential digestion with restriction enzymes such as ECoRl and SalI; and with BspMI and BamHI; as well as the fragment which codes for the polypeptide of formula I. The sequences illustrated in FIGS. 14 and 15 referred to above are partial cDNA sequences whilst that in FIG. 16 is the full cDNA sequence. Thus there is also provided a DNA sequence which comprises substantially the DNA sequence set forth in FIG. 14 or 16 or its complementary strand.

The degeneracy of the genetic code allows substantial freedom in the choice of codons which can be used to construct a gene for the appropriate polypeptide of the present invention. Codons are normally selected which are preferred by the host.

Polynucleotide probes may be constructed which are capable of hybridisation to any portion of the aforementioned DNA sequence or of a corresponding RNA or cDNA sequence. It will be appreciated that the nucleotide probe will comprise a nucleotide sequence capable of hybridisation to a sufficient length of the sequence to be determined to ensure that the probe unambiguously detects the sequence of interest. In general, the probe will be capable of hybridising to at least 8 consecutive nucleotides of the sequence to be determined.

Thus, according to a further feature of the present invention there is provided a polynucleotide probe which comprises a nucleotide sequence capable of hybridising to a DNA sequence as hereinbefore defined, or a fragment thereof, or a corresponding RNA sequence, said probe optionally having a labelled or marker component.

The polynucleotide probes of the present invention may be labelled or marked according to techniques known in the art, for example 32P-radiolabelled in any conventional way, or alternatively radiolabelled by other means well known in the hydridisation art for example to give $^{35}$S-radiolabelled probes. The probes may for example carry fluorescent markers. They may alternatively be labelled with biotin or a similar species by the method of D C Ward et al, as described in Proceedings of the 1981 ICN-UCLA Symposium on Development Biology using Purified Genes held in Keystone, Colo. on Mar. 15–20, 1981 vol. XXIII 1981 pages 647–658 Academic Press; Editor Donald D Brown et al or even enzyme-labelled by the method of A D B Malcomn et al, Abstracts of the 604th Biochemical Society Meeting, Cambridge, England (meeting of Jul. 1, 1983).

According to a further feature of the present invention there is provided an antibody effective to bind at least a fragment of a polypeptide as hereinbefore defined. The term antibody as used herein, unless the context dictates otherwise, is to be taken to include intact antibodies such as polyclonal and monoclonal antibodies and antibody fragments as well as chimeric antibodies such as described in UK Patent Application No. 2,188,638. The term "fragments" as used herein, unless qualified so as to indicate otherwise, is to be taken to refer to fragments which contain the binding region of the antibody. Such fragments may be Fab-type fragments which are defined as fragments devoid of the Fc portion, eg. Fab, Fab$^1$, and F(ab$^1$)$_2$ fragments, or may be so-called "half-molecule" fragments obtained by reductive cleavage of the disulphide bonds connecting the heavy chain components in the intact antibody.

The antibody of the present invention may if desired carry a label or marker component for example as hereinbefore described in relation to the polynucleotide probes of the present invention. Thus the antibodies may for example carry a fluorescent marker. It is not however necessary that the antibody of the present invention carry a label or marker component. Thus for example the antibody of the present invention may be detected by a second antibody which is an antibody to antibodies of the species of the antibodies of the present invention. The second antibody will have a labelled or marker component.

Such antibodies or probes may be used to detect the presence or indicate the absence of a polypeptide as hereinbefore defined or corresponding DNA or RNA as appropriate, and hence the presence or absence of material possessing inhibitory activity against elastase. Thus the probes or antibodies may be used to indicate whether an elastase-mediated condition may be at least partly caused by an absence of elastase inhibitory material.

The potency of polypeptides of the present invention to act as an elastase inhibitor was determined by the ability of a compound of the invention to inhibit the action of human leukocyte elastase (HLE) on a low molecular weight peptide substrate. The potency of an inhibitor was evaluated by obtaining a kinetic determination of the dissociation constant, $K_i$, of the complex formed from the interaction of th inhibitor with HLE. The substrate used was the anilide methoxysuccinyl-alanyl-alanyl-prolyl-valine-p-nitroanilide as described by K. Nakajima et al. in the *J. Biol. Chem.*, 254: 4027–4032 (1979) and by T. Teshima et al. in *J. Biol Chem.*, 257: No 9, 5085–5091 (1982). The HLE enzyme used in these studies may be obtained from Elastin Products of St. Louis, Mo. or can be purified according to B. R. Viscarello et al. in *Preparative Biochemistry*, Vol. 13, pages 57–67, (1983).

The polypeptides as hereinbefore defined may be used as obtained or purified in a known and appropriate manner and formulated into pharmaceutical compositions, for example by admixture with a pharmaceutically acceptable diluent or carrier. Administration may be by way of various routes known in the art. In particular, administration may be effected parenterally, for example intra-nasally, rectally, pulmonary, and by way of injection such as by way of intramuscular or subcutaneous injection. The pharmaceutical compositions will be formulated according to the mode of administration to be employed. For example, when the composition is to be administered intra-nasally, the composition may be formulated as a powdered aerosol; and when the composition is to be administered by way of injection it may be formulated as a sterile solution or suspension. Suitable diluents include aqueous solutions and additives such as buffers and surfactants may be added.

Pharmaceutical compositions of the present invention also include controlled release formulations. For example, the polypeptides of the present invention may be encapsulated in a biodegradable polymer, or may be dispersed in a matrix of such a polymer, so that the polypeptide is released as the degradation of the polymer matrix proceeds. Suitable biodegradable polymers for use in sustained release formulations include polyesters which gradually become degraded by hydrolysis when placed in an aqueous, physiological environment. A particular pharmaceutical composition which provides for extended release of a polypeptide is described in European Patent No. 58481. In this composition a polylactide is employed, and when placed in an aqueous physiological-type environment polypeptide is released from the composition in a continuous manner until essentially all of the polypeptide has been released.

The polypeptides of the present invention are potentially useful in the treatment of conditions in which elastase-mediated tissue proteolysis plays a role.

The polypeptides of the present invention (as herein defined) may be administered to a warm-blooded animal in need thereof, particularly a human, for the treatment of inflammatory conditions, pulmonary conditions, skin conditions and conditions involving mucous secretion. Examples of conditions in which the polypeptides of the present invention are of potential use include atherosclerosis, arthritis, emphysema, adult respiratory syndrome, cystic fibrosis, bronchitis, acute non-lymphobastic leukemia and psorasis.

The present invention also provides the use of a polypeptide (as herein defined) or an analogue thereof in the manufacture of a medicament for treating diseases such as these mentioned above.

Thus the present invention also provides a method of treating a warm-blooded animal, for example man, which comprises administrating an effective amount of a polypeptide of the present invention (as hereinbefore defined) or an analogue thereof to said warm-blooded animal in order to treat diseases such as those mentioned above.

The invention will now be further illustrated, by way of example only, by the following Examples with reference to the accompanying drawings, in which:

FIG. 6 illustrates an isoelectric focussing procedure used to determine the isoelectric point of the polypeptide of formula I;

FIG. 13 illustrates a DNA sequence used in obtaining expression of the polypeptide of formula I;

FIGS. 14 and 15 illustrate partial cDNA sequences for the polypeptide of formula I;

FIG. 16 illustrates the cDNA sequence for the polypeptide of formula I;

FIG. 19 illustrates the accumulation of polypeptide of formula I in yeast.

ISOLATION OF HUMAN LEUKOCYTE ELASTASE INHIBITOR

Scales from the skin of patients with psoriasis or atopic dermatitis were collected, pooled and extracted in batches of between 1 and 100 g. The scale material, which included normal human callus, was suspended in aqua dest. (10 to 200 ml), the pH of the suspension adjusted to pH 2.8 using 1% citrate and formic acid, diluted with 10 volume per cent ethanol and frozen (−80° C.). Mechanical disruption was then carried out by ultraturrax (1 hour on ice), ultrasound (15 minutes, 400 watts), ultraturrax (1 hour) and centrifugation (10 minutes at 5,000×g). The sediments obtained were re-extracted with 50% ethanol and with 50% citrate/formiate (pH 3.0) and the supernatants of both extractions were combined. The combined extracts were concentrated by ultrafiltration (Amicon YM5) and diafiltrated against 0.01M ammoniumformiate (pH 4.0) to yield crude extract.

Purification

The crude extract obtained by the isolation procedure described above was purified chromatographically (according to the procedures described below) to yield a homogeneous sample of material possessing inhibitory activity against human leukocyte elastase.

Figure 1:
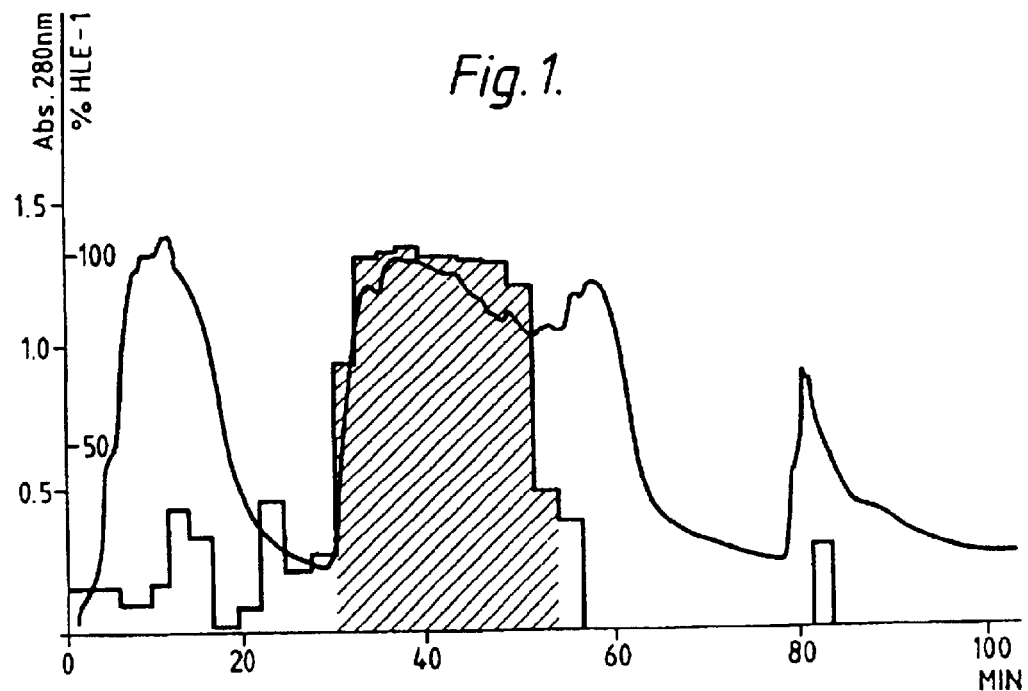
FIG. 1 illustrates a cation-exchange chromatographic procedure used in the extraction and purification of the polypeptide of formula I from psoriatic plaques.
Figure 2:
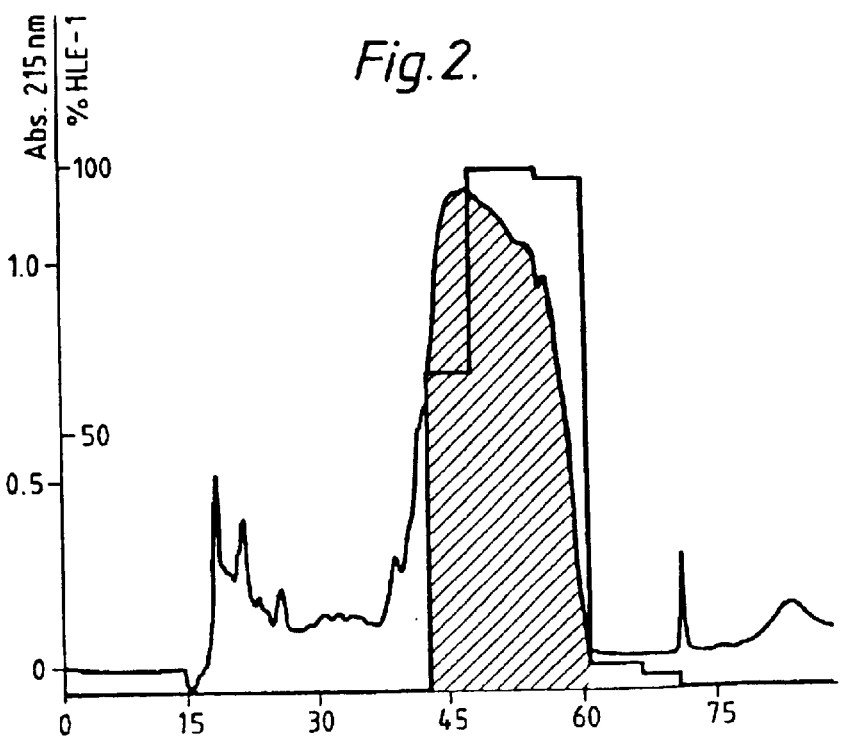
FIG. 2 illustrates a reversed-phase-C8-chromatographic procedure used in the extraction and purification of the polypeptide of formula I from psoriatic plaques.

The crude extract was initially purified by way of cation exchange HPLC to separate material possessing inhibitory activity against human leukocyte elastase from material such as human leukocyte elastase itself. As illustrated in FIG. 1, material possessing inhibitory activity against HLE was eluted as a broad peak between about 26 and 58 minutes. The fractions containing the prominent inhibitor were further purified on a $C_8$-reversed-phase column and rechromatographed until approximate homogeneity was observed (FIG. 2).

Figure 4:
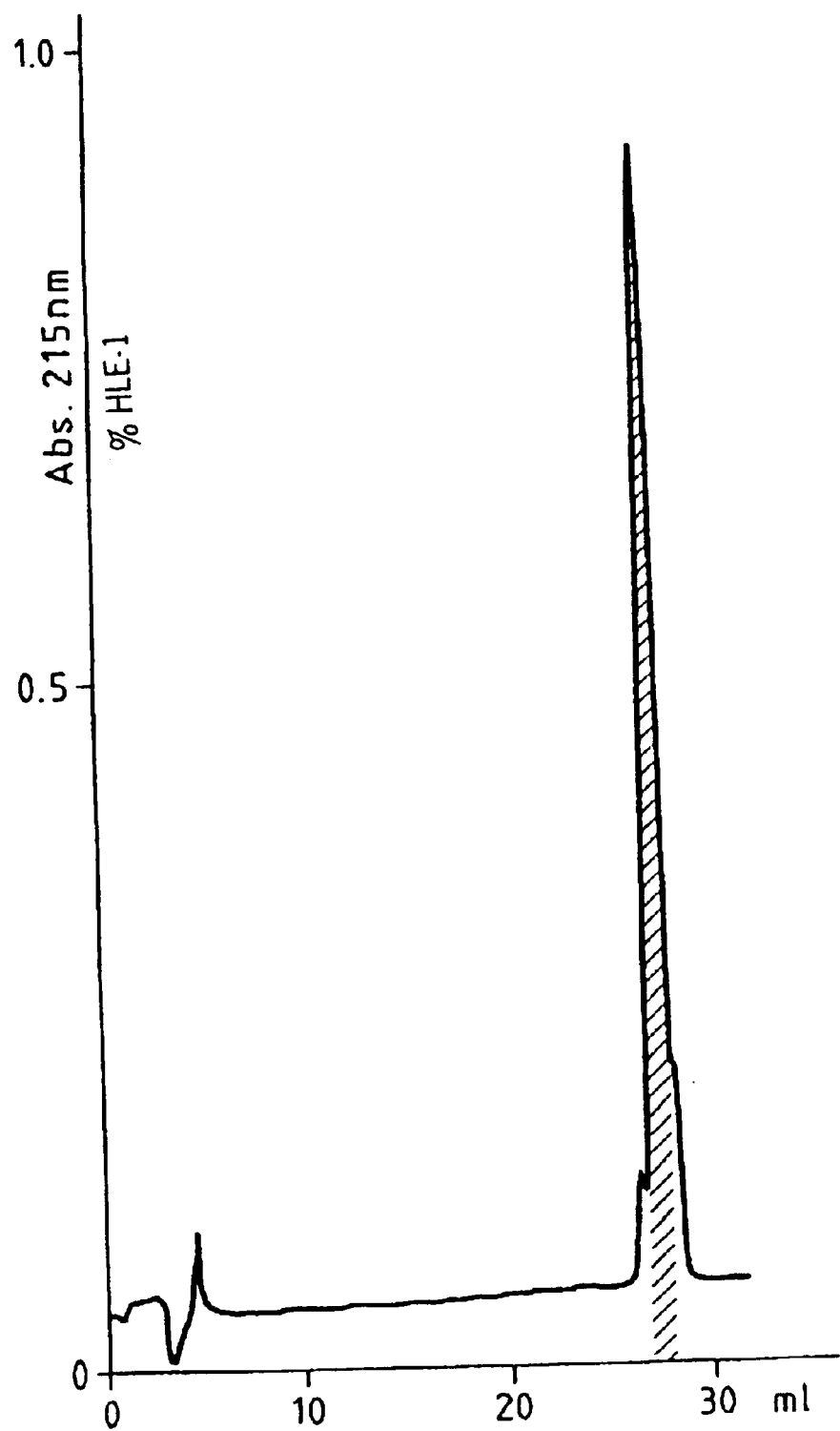
FIG. 4 illustrates a reversed-phase-$C_{18}$-chromatographic procedure used in the extraction and purification of the polypeptide of formula I from psoriatic plaques.

Those fractions containing material possessing inhibitory activity against HLE were combined and the chromatographed on a Poly LC column. The separation yielded material which included a component which was shown to be the prominent inhibitor. This component was further purified by $C_{18}$-reversed-phase chromatography (FIG. 4). In some preparations additional chromatogrphic steps of size exlusion HPLC and reversed-phase Poly F-HPLC were necessary in order to obtain greater than 95% purity (as proved by analytical runs on $C_{18}$-reversed-phase chromatography, Poly LC and by complete absence of contaminats in SDS-PAGE and isoelectric focussing).

Cation Exchange—HPLC

Column: TSK CM 3-SW (7.5×150 mm, LKB Bromma, Sweden)

Run: 20 minutes buffer A with a flow rate of 0.5 to 1.0 ml per minute;

30 minutes linear gradient to 100% buffer B with a flow rate of 1.0 ml per minute; 20 minutes buffer B; and 50 minutes buffer C.

Buffer A: 0.01M ammoniumformiate pH 4.0
Buffer B: 0.5M ammoniumformiate pH 4.0
Buffer C: 0.5M ammoniumformiate pH 3.0

The crude extract was chromatographed under the above conditions with automatic collection of 60 drops per fraction and with UV-detection at 280 nm. Those fractions containing material possessing inhibitory activity eluted by the gradient were combined, concentrated and drafiltrated against 0.1% TFA.

Reversed-Phase-$C_8$-HPLC

Column: Nucleosil 300-7 $C_8$-HPLC Column (250×14.7 mm, Macherey-Nagel, Duren, Germany)

Run: Flow rate-3 ml per minute 20 ml 20% buffer B; 75 ml linear gradient to 60% buffer B;

15 ml linear gradient to 100% buffer B; 30 ml 100% buffer B

Buffer A: 0.1% TFA

Buffer B: 0.1% TFA in acetonitrile

Samples were chromatographed under the above conditions with UV-detection at 215 nm and with peakwise collection. Fractions containing material possessing inhibitory activity eluted with the gradient up to 60% buffer B were combined, lyophilized and rechromatographed on the same column and under identical conditions.

Poly-(2-Sulphoethyl Aspartamide)-HPLC

Column: Poly LC column (200×4.6 mm, Columbia, Md., USA)

Run: flow rate 1 ml per minute 10 ml buffer A; 30 ml linear gradient to 50% buffer B; 10 ml linear gradient to 100% buffer B; 10 ml buffer B Buffer A: 5 mM $KH_2PO_4$, pH 3.1+25% acetonitrile Buffer B: 5 mM $KH_2PO_4$, 0.5M KCl, pH3.1+25% acetonitrile Lyophilized samples were solubilised in buffer A and then chromatographed under the above conditions, with UV detection at 220 nm and with peakwise collection.

Reversed-Phase-$C_{18}$-HPLC

Column: Nucleosil 100-5 $C_{18}$ (250×4.6 mm, Bischoff, Leonberg, Germany).

Run: flow rate 1 ml per minute 30 ml linear gradient from 10 to 40% buffer B;

10 ml linear gradient to 100% buffer B; 10 ml buffer B

Buffer A: 0.1% TFA

Buffer B: 0.1% TFA in acetonitrile

Samples were chromatographed under the above conditions with UV-detection at 215 mm and with peakwise collection. If necessary, fractions containing material possessing inhibitory activity were rechromatographed in the same system until homogeneity was achieved.

Size-Exclusion-HPLC

Column: TSK 2000 column (600×7.5 mm, LKB, Bromma, Sweden)

Run: flow rate 1 ml per minute 0.1% TFA

Samples were chromatographed under the above conditions with UV-detection at 215 mm and with 20 drops collected per fraction. Mr was calibrated using the peptides Val-gly-ser-glu, insulin, B-chain fragment 22–36, aprotinin, chicken egg albumin and bovine serum albumin.

Reversed-Phase-Poly F-HPLC

Column: Poly F column (80×6.2 mm, Du Pont, Dreieich, Germany)

Run: flow rate 1 ml per minute 30 ml linear gradient from 10% buffer B to 40% buffer B;

2 ml linear gradient to 100% buffer B; 10 ml buffer B.

Buffer A: 1% $NH_4$

Buffer B: 1% $NH_4$ in acetonitrile

Lyophilized samples were solubilized in buffer A and chromatographed under the above conditions with UV-detection at 215 mm and with peakwise collection.

Protein Determination

Protein concentrations were determined by integration of the absorbance at 215 mm in Reversed-Phase-$C_{18}$-chromatography. The following were used as calibrators: ubiquitin (Sigma) and recombinant eglin C (Ciba-Geigy).

SDS-PAGE

Sodium dodecyl sulphate polyacrylamide gel electrophoresis (SDS-PAGE) was performed using a Pharmacia Phast System (Pharmacia, Freiburg, Germany) and homogeneous 20% SDS-gels according to the manufacturer's instructions. Samples were lyophilized and reduced by boiling (5 minutes) in 0.01M $H_3PO_4$, 8M urea, 2.5% SDS, 0.02% bromophenol blue, pH 6.8. As standards, myoglobulin fragments (Pharmacia) or horse myoglobin (Serva) and ubiquitin (Sigma) were used. Silver stains were performed according to the manufacturer's instructions (Sigma).

Isoelectric Focussing

Isoelectric focussing was performed by using Servalyt Precoates pH 3–10 and Test-Mix 9 (Serva). Prefocussing was for 30 minutes at 3 watts, and silver stain (Sigma) or Comassie blue R stain was used according to Serva instructions. In parallel, the precoates were sliced and eluted to localise inhibitory active peptides. Approximately 1 mm slices were eluted with 100 μl acetonitrile. The eluates were allowed to dry and were resolved in 100 μl of buffer (0.1M HEPES, 0.5M NaCl, 1% BSA, pH 7.5) containing 20 ng HLE. After 30 minutes incubation the remaining HLE activity was determined.

Biological Properties

The inhibition of several proteases by the prominent inhibitor were determined according to the methods described below. The results are illustrated in Table 1.

TABLE 1

| PROTEASE | DISSOCIATION CONSTANT ($K_i$) | SUBSTRATE |
|---|---|---|
| human leukocyte elastase | $3 \times 10^{-10}$M | 2 mM AAPVpNA |
| porcine pancreatic elastase | $1 \times 10^{-9}$M | 0.1 mM AAPV-AFC |
| human cathepsin G | n.i. | 0.5 mM AAPFpNA |
| Alpha-chymotrypsin | n.i. | 0.5 mM AAPFpNA |
| trypsin | n.i. | 0.1 mM TGPLpNA |
| plasmin | n.i. | 0.1 mM TGPLpNA |

(n.i.: no inhibition)

Inhibition of Human Leukocyte Elastase

The activity of human leukocyte elastase (EC 3.4.21.37) was determined according to the method of Nakajima et al (7). Inhibition of HLE was determined by the use of the synthetic peptide methoxy-succinyl-alanyl-alanyl-prolyl-valyl-p-nitro anilide (AAPVpNA, Sigma).

Sample (100 μl) and 100 μl HLE (200 ng/ml; Elastin Products Corporation, Pacific, Mo., USA) in assay buffer (0.1M, HEPES, 0.5M NaCl, 10% DMSO, pH 7.5) were incubated for 30 minutes at room temperature. Substrate (800 μl 0.5 mM) in assay buffer was then added.

Changes in absorbance at 405 nm were followed up to 1 hour and the %-inhibition was calculated from the remaining activity and controls. The dissociation constant (Ki) was determined according to the method of Green and Work (8) in the same system, using 2 mM substrate and (1 μg/ml) HLE (final concentrations).

Inhibition of Porcine Pancreatic Elastase

The activity of porcine pancreatic elastase (E.C. 3.4.21.36) was determined using the flourogenic substrate methoxy-succinyl-alanyl-alanyl-prolyl-valyl-trifluoromethylcoumarine (AAPV-AFC, Bachem, Bubendorf, Switzerland).

Elastase (100 μl) and inhibitor (100 μl) were preincubated for 30 minutes. A solution of substrate (1.8 ml of a 0.1 mM solution) was then added. Flourescence, Ex 400 Em 505, was followed and the %-inhbition was calculated from the initial activity of samples and controls. The dissociation constant (Ki) was determined according to the method of Green and Work (8).

Inhibition of Cathepsin G and Alpha-Chymotrypsin

The activities of cathepsin G and Alpha-chymotrypsin were determined according to the method of Nakajima et al (9) using an analogue to HLE—succinyl-alanyl-alanyl-prolyl-phenylalanyl-p-nitroanilide (AAPFpNA, Sigma). For inhibition experiments, the highest concentration of the inhibitor was 1 μg/ml, representing a threefold molar concentration as compared to cathepsin G and Alpha-chymotrypsin.

Inhibition of Trypsin and Plasmin

100 μl inhibitor (1 μg/ml) and 100 μl trypsin (1 μg/ml) or plasmin (1 μg/ml) as appropriate were incubated for 30 minutes before adding the substrate, 0.1 mM tosyl-glycyl-prolyl-lysin-pNA (Boehringer Mannheim, FRG) in 0.05M HEPES, 0.12M NaCl, pH7.5.

Inhibition of Proteinase 3

Proteinase 3 was purified from human polymorphonuclear leukocytes using the method of Ludemann reported in J Exp Med 171, 357–362, 1990. The absence of human leukocyte elastase and cathespin G was confirmed by the lack of activity of the proteinase 3 preparation with the substrates methoxy-succinyl-ala-ala-pro-val-p-nitroanilide (AAPVpNA), and succinyl-ala-ala-phe-p-nitroanilide respectively according to the method of Nakajima (7).

The elastinolytic activity was determined by hydrolysis of bovine ligamentum nuchae elastin-FITC (Elastin Products Corporation, USA).

The proteinase 3 preparation (1 μl) was preincubated at 37° C. for 30 minutes with the elastase inhibitor of formula I (0–1 μg) in carbonate buffer (50 μl, 0.1M), NaN$_3$ (0.02%), Brij 35 (0.01%), pH8,5. Elastin-FITC (1 mg) in carbonate buffer (100 μl, 0.1M), NaN$_3$ (0.02%), Brij 35 (0.01%), pH8.5. The mixture was incubated at 37° C. with gentle agitation for 4 hours, and then centrifuged at 6000×g. The supernatants were diluted 1:20 and the fluorescence of the solubilised elastin-FITC was determined using a Perkin Elmer LS 50 microtiterplate reader at Ex489 nm, Em 513 nm. Fluorescence was corrected by enzyme free controls and inhibition expressed in % of inhibitor free controls.

The polypeptide of formula I was found to be a potent inhibitor of protinase 3, with an activity corresponding to an $IC_{50}$ of $9.5 \times 10^{-9}$M.

Characterization

Figure 5:
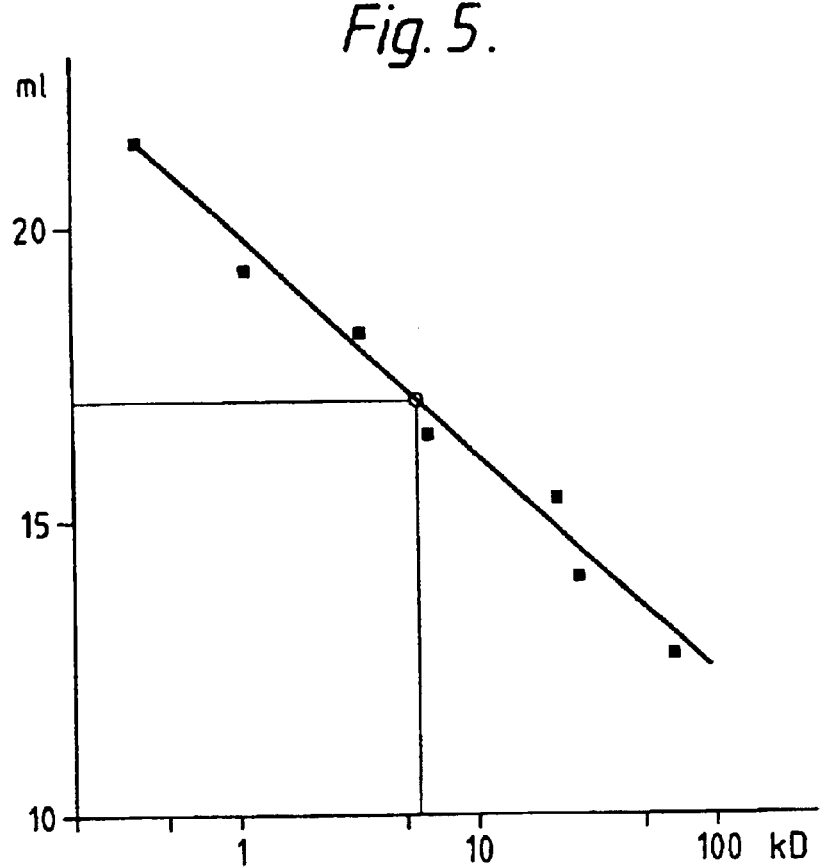
FIG. 5 illustrates an analytical gel chromatographic procedure used to determine the molecular weight of the polypeptide of formula I.

Analytical size-exclusion chromatography (Tsk 2000) of the prominent inhibitor gave an apparent molecular mass of between 5 and 10 KD) (FIG. 4). The molecular mass of the prominent inhibitor on SDS-PAGE was about 9 KD), with migration in close proximity of ubiquitin (MW 8500) as shown in FIG. 5.

The isoelectric point of the prominent inhibitor was found to be pH 9.7, as shown by silver stain and by parallel enzymatic detection of the inhibitor in gel slices (FIG. 6).

Figure 7:
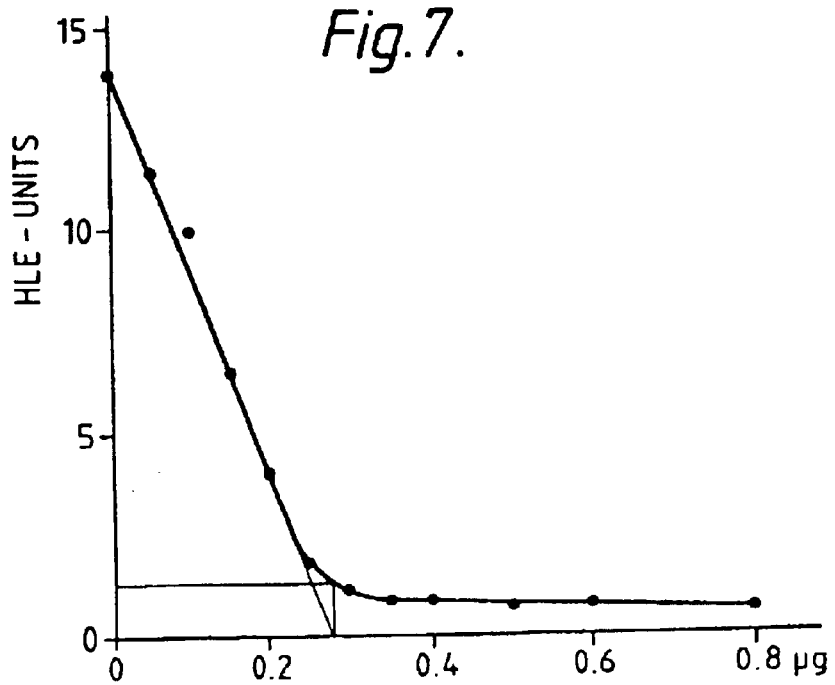
FIG. 7 illustrates the titration of human leukocyte elastase with the polypeptide of formula I.

The prominent inhibitor was found to inhibit the serine elastases HLE and porcine pancreatic elastase. However, neither Alpha-chymotrypsin, nor trypsin and plasmin were significantly inhibited by an at least threefold excess of the inhibitor. The equilibrium dissociation constant (Ki) for the inhibition of HLE was determined according to the method of Green and Work (8), as shown in FIG. 7.

The inhibitor was also found to be acid stable.

Structure Determination of HLE Inhibitor

Direct Sequencing

Figure 8:
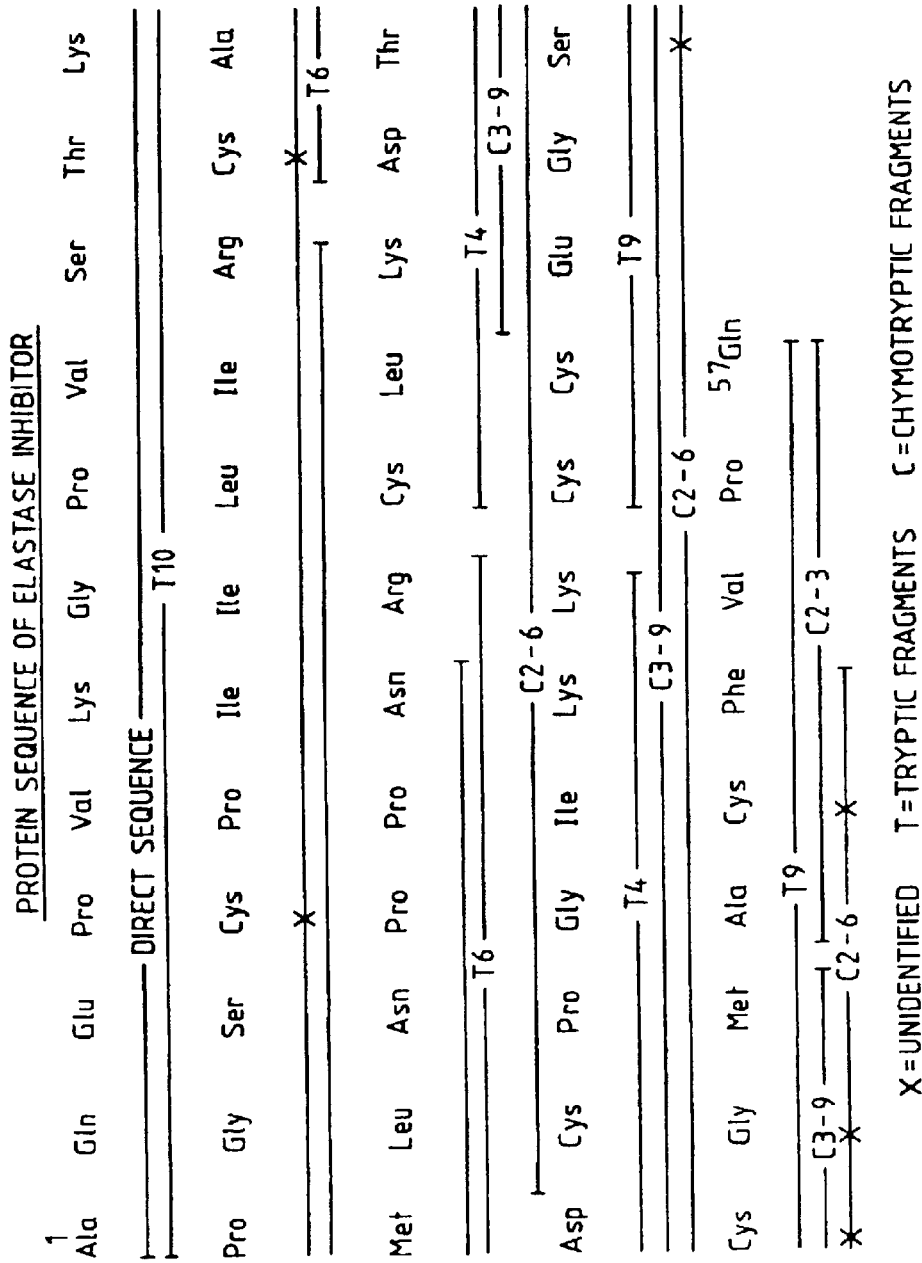
FIG. 8 shows the sequence of the polypeptide of formula I ("the prominent inhibitor")

Approximately 5 μg of the purified material of the prominent inhibitor was subjected to sequence analysis using an Applied Biosystems Model 470A Gas Phase Sequencer with Model 120A on line analysis of the phenylthiohydantoins. This gave a sequence of thirty residues as shown in FIG. 8 but with cysteines inferred by the absence of any identified residue. The initial yield of amino acid residues was compatible with a single chain polypeptide of molecular size 6–8K daltons.

Carboxamidomethylation (CAM)

Figure 9:
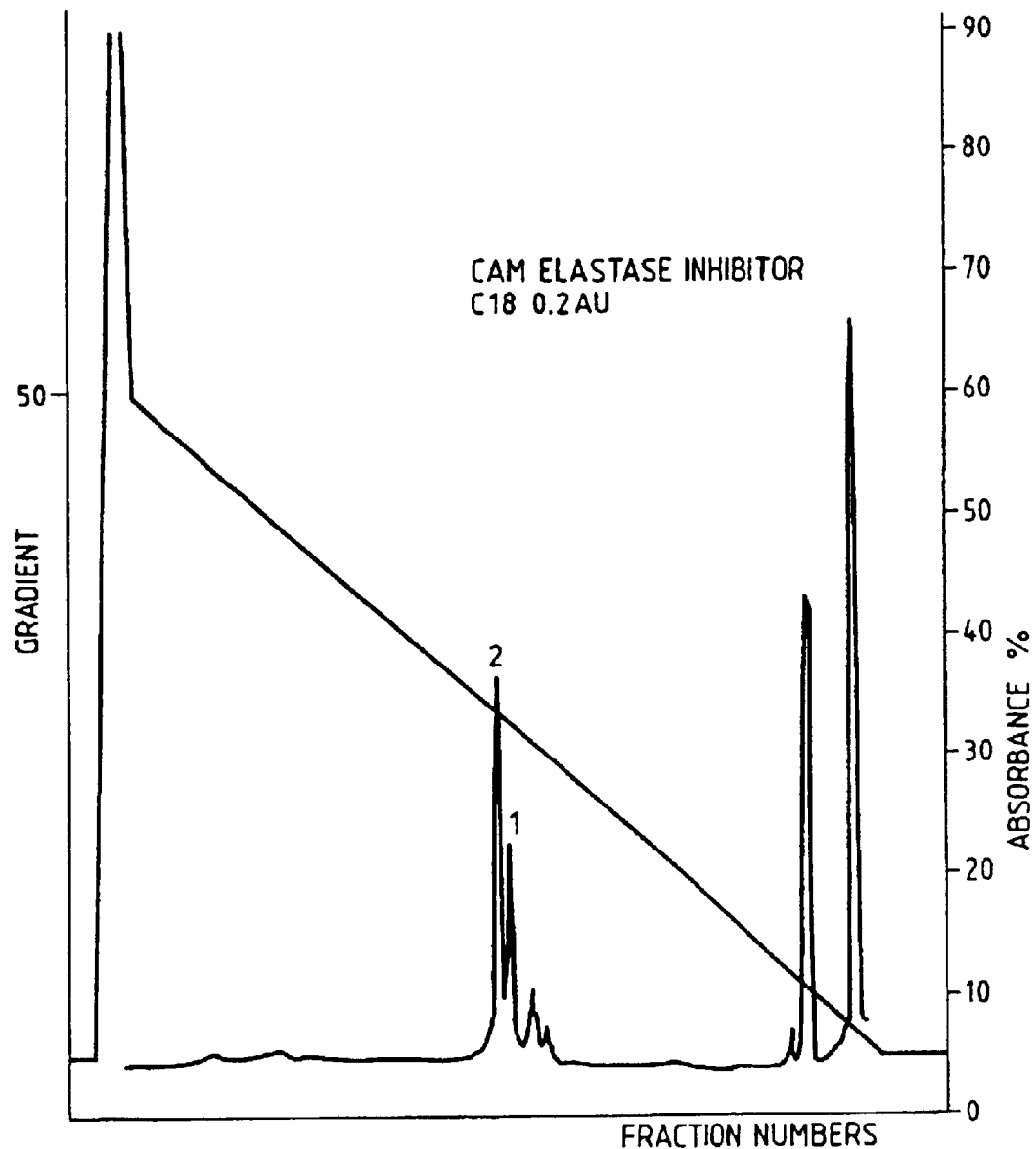
FIGS. 9 to 12 illustrate the procedure used to sequence the prominent inhibitor (the polypeptide of formula I)

The purified prominent inhibitor (10 μg) was dissolved in water (50 μl) and mixed with 6M guanidine hydrochloride, 0.1M tris hydrochloride pH8.5 buffer (30 μl). The tube was flushed with nitrogen and a dithiothreitol solution added (5 μl of a 50 mg/ml solution in guanidine buffer). The tube was again flushed with nitrogen, sealed and kept at 37° C. for 4 hours. Iodoacetamide (5 mg) in guanidine buffer (50 μl) was added and after flushing with nitrogen again the tube was kept in the dark at ambient temperature for 1 hour. The sample was diluted to 1 ml with 0.1% aqueous trifluoracetic acid and applied directly to a Vydac C18 column (25×0.46 cm). The column was developed at 1 ml/min with a linear gradient from 0.1% trifluoracetic acid in water to 0.1% trifluoroacetic acid in acetonitrile over 70 minutes. This gave two peaks (FIG. 9), a minor component at fractions 33–34 and a major one (ca. 67%) at 35–36. Each component was separately exposed again to the carboxamidomethylation conditions but further chromatography showed they were unaltered thus showing that original reaction had gone to completion.

Amino Acid Analysis

Half of the minor component from the carboxamidomethylation was hydrolysed with 6 N hydrochloric acid containing 1% phenol in vacuo at 110° C. for 16 hours. The hydrolysate was analysed using an LKB Alpha plus amino acid analyser and gave ratios as shown in table 2. Although the sample analysed was very small, background correction was not applied.

TABLE 2

| Amino Acid | Ratio based on 57 AA peptide | AAs found in sequenced peptide |
|---|---|---|
| Asp/Asn/Cys | 8.8 | 4 + 8 cys |
| Thr | 2.1 | 2 |
| Ser | 4.5 | 3 |
| Glu/Gln | 5.5 | 4 |
| Pro | 7.0 | 8 |
| Gly | 7.4 | 5 |
| Ala | 3.0 | 3 |
| Val | 3.0 | 3 |
| Met | 1.6 | 2 |
| Ile | 2.8 | 4 |
| Leu | 3.4 | 3 |
| Phe | 1.1 | 1 |

TABLE 2-continued

| Amino Acid | Ratio based on 57 AA peptide | AAs found in sequenced peptide |
|---|---|---|
| Lys | 4.5 | 5 |
| Arg | 2.3 | 2 |

Figure 10:
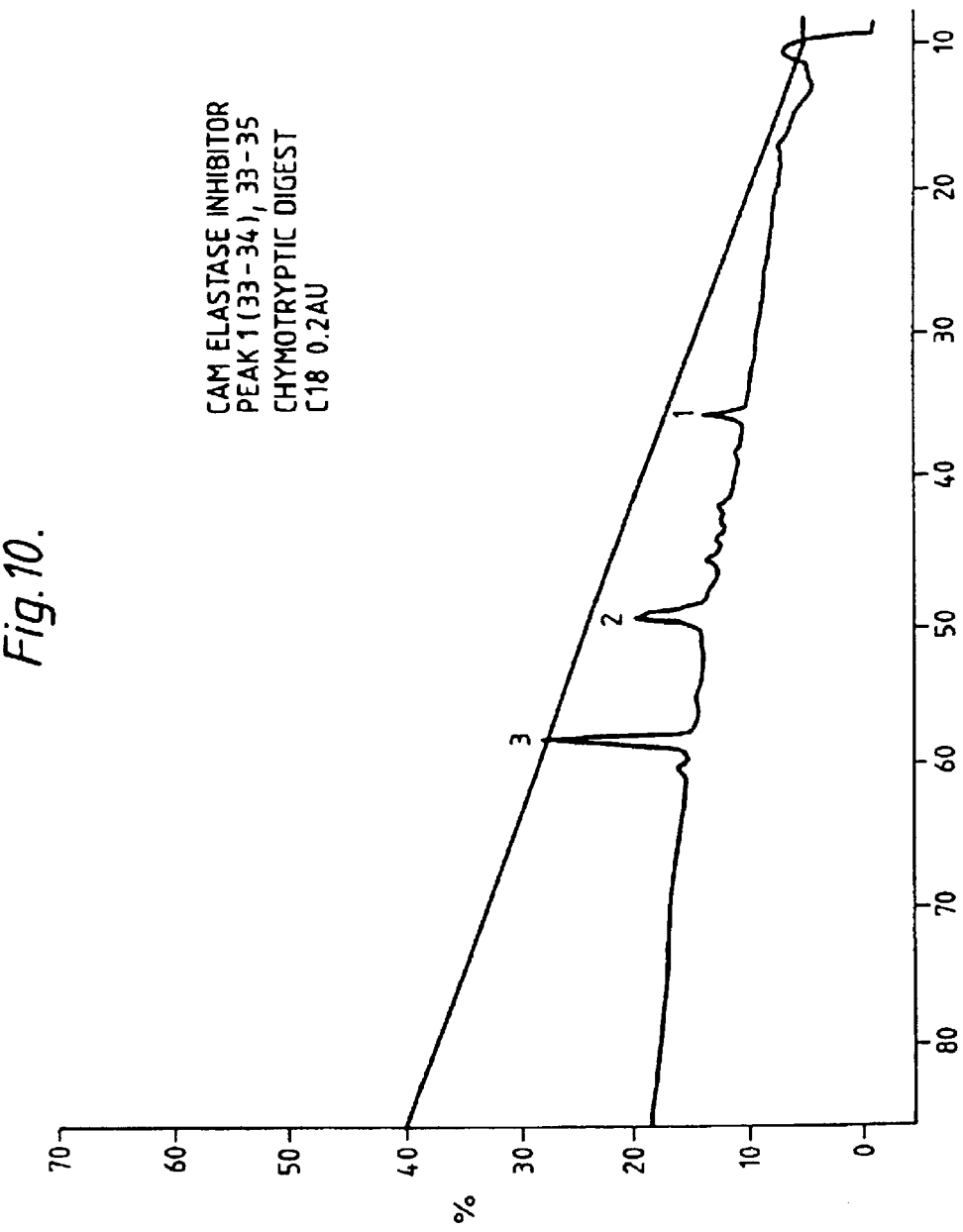
Figure 11:
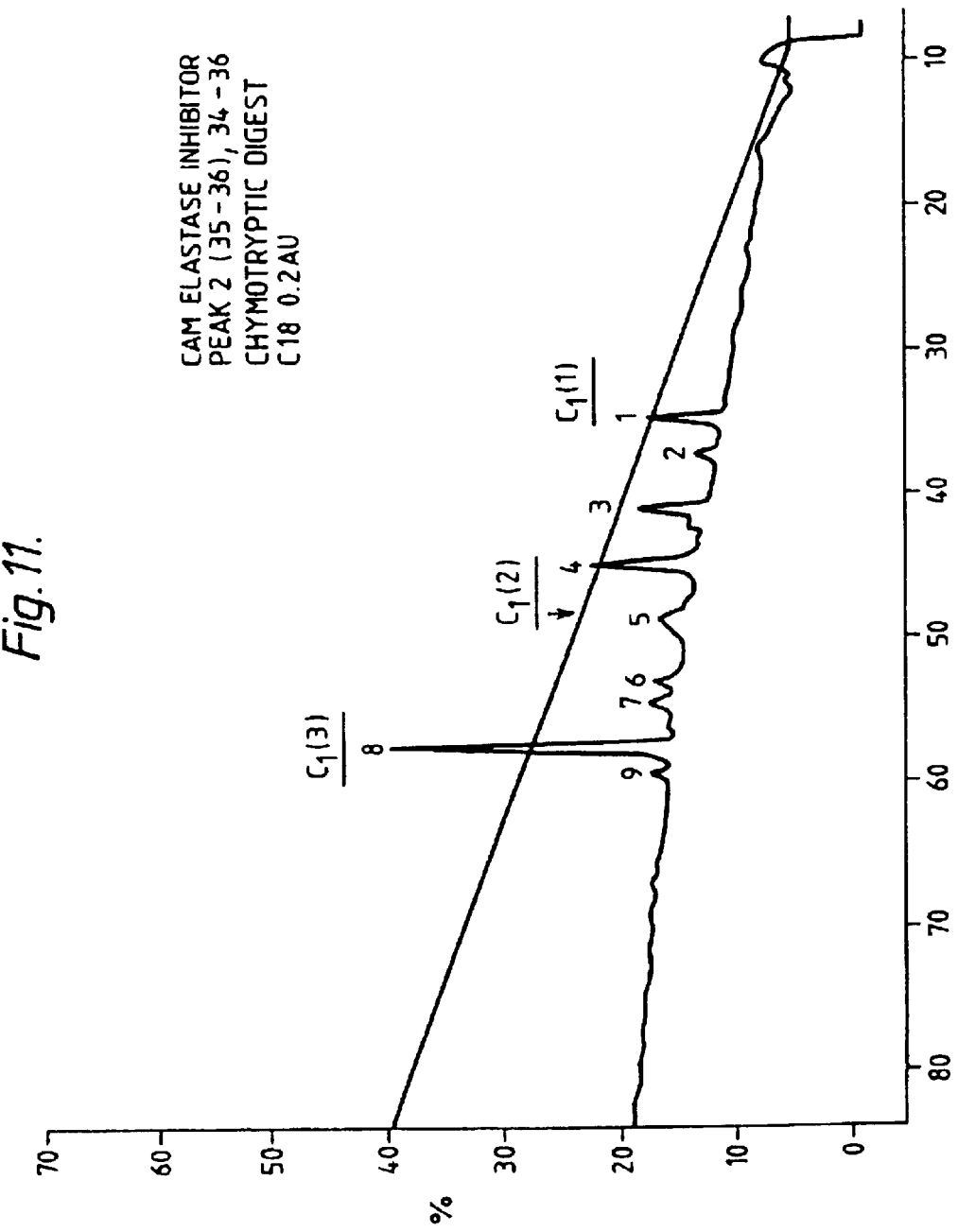
Figure 12:
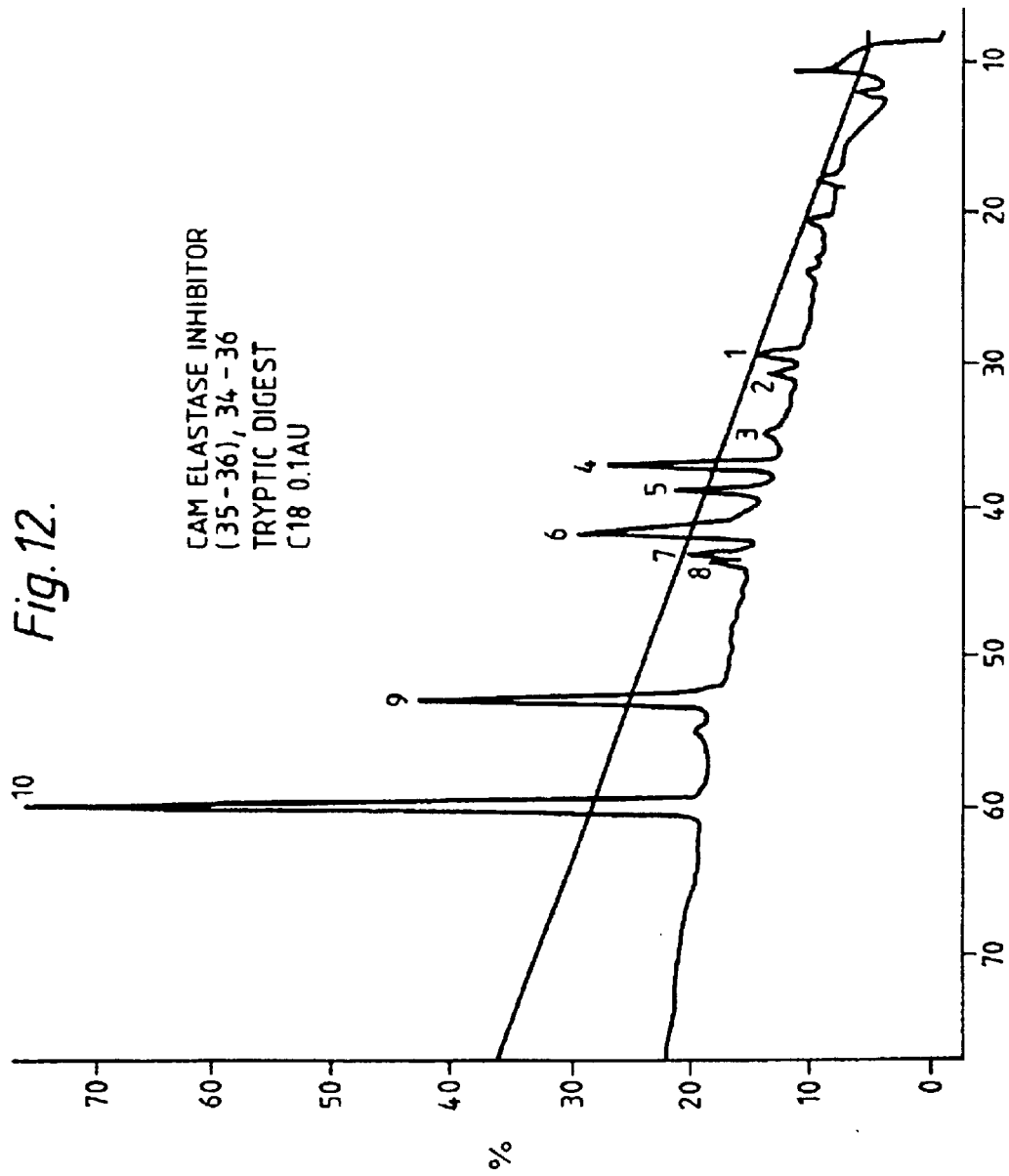
Figure 17:
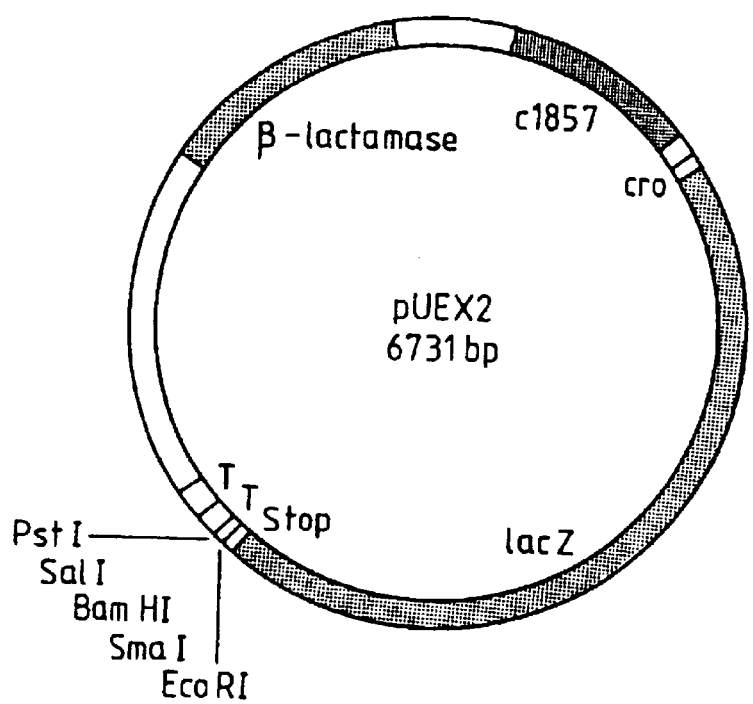
FIG. 17 illustrates the plasmid pUEX2.

Digestion with Chymotrypsin $C_1$: The remaing half of the CAM derivative in fractions 33–34 was taken up in 0.1M ammonium bicarbonate (50 μl) and 0.2M calcium chloride (1 μl) and treated with chymotrypsin (Worthington, 10 μl of a 20 μg/ml solution). The solution was kept at 37° C. for 1 hour and then diluted with 0.1% trifluoracetic acid in water (200 μl) for loading directly on to a Vydac $C_{18}$ column. A linear gradient to 0.1% trifluoroacetic acid in acetonitrile was run over 60 minutes at a rate of 1 ml/min. This gave three main peaks as shown in FIG. 10. Each of these was sequenced as far as possible and the results are given below. $C_2$: Half the CAM product in fractions 35–36 were digested with chymotrypsin under the same conditions. The HPLC profile (FIG. 11) showed content which helped selection of enzymes for degradation into smaller fragments.

Direct sequencing gave the first 30 residues and this was confirmed by the large tryptic fragment T10. The trypsin conditions allowed for large fragments on the major products, i.e. not all lysine bonds were broken and those fragments encompassing the full structure are given in FIG. 8. Break points were limited to basic residues.

By contrast chymotrypsin did not cleave after the one aromatic residue but did after the two methionines and also after leucine −33. In addition, cleavage occured after leucine −20.

The C-terminal glutamine was assigned on the basis of a very small but detectable residue found in both the T9 and C2-3 peptides following strong proline peaks. This may however be anticipated from such a C-terminal residue. Several other chymotryptic peptides, not included in FIG. 8, provided further confirmation of the structure.

The chymotryptic digest from the smaller CAM derivative were sequenced as far as possible giving the following data:

```
C1-1 (cf C2-1)      Ile-Arg-Cys-Ala-Met
C1-3 (cf C2-8)      Ala-Gln-Glu-Pro-Val-Lys-Gly-Pro-Val-Gly/Ser-Xaa-
                       Lys-Pro-Gly-
C1-2                Leu-Asn-Pro-Pro-Asn-Arg-Cys-Leu-Lys-Asp-Thr-Asp-
                    Cys-Pro-Gly-Ile-Lys-Lys-Cys-Cys-Gly/Glu-Gly-Ser-Cys-
``` more extensive degradation had occured although peaks 1 and 3 (FIG. 10) appeared to be present to the same extent as peaks 1 and 8 of the second digest. The other peak, 2 in FIG. 10, was relatively much smaller in the second digest and not clearly at the same position as were the other two. The additional peaks from $C_2$, i.e. 3, 4, 6, 7 and 9 were sequenced. These are shown (FIG. 8) apart from peak 7 which proves to have the same sequence as 6 as far as it was taken.

Digestion with Trypsin

T: The remaining portion of the main CAM derivative, fractions 35–36, was taken into 0.1M ammonium bicarbonate (50 μl) and 0.2M calcium chloride (1 μl) and treated with trypsin (200 ng in 10 μl 01M ammonium bicarbonate). The solution was maintained at 37° C. for 30 minutes, diluted with 0.1% aqueous trifluoroacetic acid and loaded immediately on to a $C_{18}$ column which was developed as for the other enzyme digests (FIG. 5). This showed two definable product peaks and no starting material remaining. The relevant sequence data is shown (FIG. 1).

A single amino acid analysis was carried out which gave an approximate rather than accurate indication of amino From the data available the differences between the major and minor CAM derivatives could not be seen. It was not due to any extension or deletion at the N-terminus.

The structure established (FIG. 8) is that of a small predominantly basic polypeptide. It has an unusually high content of proline for such a molecule and also the glycine and cysteine indicate a tightly caged molecule.

In addition to the prominent inhibitor, comprising a 57 residue polypeptide, further material possessing inhibitory activity against human leukocyte elastase was isolated and polypeptides therein partially sequenced. The following results were obtained:

Peak II—Major component E
   Minor component D
Peak III—Major component D
   Minor component E
Peak IV—Major component B
   Minor component C
Peak V—Major component A
   Minor component starts at same position as main elastase inhibitor.

```
Component A:

Asn-Gly-Gln-Asp-Pro-Val-Lys-Gly-Gln-Val-Ser-Val-Lys-Gly-Gln-
Asp-Lys-Val-Lys-Ala-Gln-Glu-Pro-Val-Lys-Gly-Pro.

Component B:

Gly/Ala-Gln/Val-Asp-Lys-Val-Lys-Ala-Gln-Glu-Pro-Val-Lys-Gly-
Pro-Val-Ser-Thr-Lys-Pro-Gly-Ser-Cys-Pro-Ile-Ile-Leu.
```

-continued

Component C:

Asp-Lys-Val-Lys-Ala-Gln-Glu-Pro-Val-Lys-Gly-Pro-Val-Ser-Thr-
Lys-Pro-Gly-Ser-Cys.

Component D:

Gly/Val-Lys-Ala-Gln-Glu-Pro-Val-Lys-Gly-Pro-Val-Ser-Thr-Lys-
Pro-Gly-Ser-Cys-Pro-Ile-Ile-Leu-Ile-Arg-Cys-Ala-Met-Leu-Asn-Pro-Pro-
Asn-Arg-Cys-Leu-Lys-Asp-Thr.

Component E:

Lys-Gly-Pro-Val-Ser-Thr-Lys-Pro-Gly-Ser-Cys-Pro-Ile-Ile-Leu-
Ile-Arg-Cys-Ala-Met-Leu-Asn-Pro-Pro-Asn.

In the above N-terminal sequences the 1–19, 1–6 and 1–4 sequences of Components A, B and C respectively were determined with less certainty than the following part of the sequence.

The additional components isolated were found to have similar properties to the prominent inhibitor, for example similar biological properties.

The material possessing inhibitory activity against human leukocyte elastase was thus found to comprise a prominent inhibitor comprising an acid-stable polypeptide which is believed to bind human leukocyte elastase in a 1:1 molar ratio. This inhibitor is believed to be bound in a cage-like structure with a number of di-sulphide bonds holding the peptide in this form. A high affinity and specificity for elastases, and in particular for HLE, renders the inhibitor useful in the treatment of conditions in which elastase-mediated tissue proteolysis plays a role, for example psoriasis and emphysema. Other polypeptides were also isolated indicating a family of polypeptides with similar properties to the prominent inhibitor and, indeed, partial sequencing of related polypeptides indicated the presence of at least a part of the amino-acid sequence of the prominent inhibitor.

Proteinase 3 is the third elastin degrading serine protease, beside human leukocyte elastase and porcine pancreatic elastase, that is effectively inhibited by the prominent inhibitor (the polypeptide of formula 1). Since this inhibits: appears to be a physiological regulator of human leukocyte elastase mediated tissue proteolysis in skin and probably in other organs it appears to be of interest that this inhibitor also inhibits proteinase 3. Both enzymes human leukocyte elastase are constituents of the azurophilic granules of neutrophils and both are able to induce emphysema like tissue destruction in hamsters after instillation of the enzyme into the airways (Kao, R. C., Wehner N. G. Skubitz, K. M, Gray B. H. J. R, Huidal, Protinase 3 A Distinct Human Polymorphonuclear Leukocyte Proteinase that produces Emphysema in Hamsters J. Clin. Invest. 82, 1963–1973, 1988). Since this inhibitor is able to inhibit either enzyme after preadsorption to the enzyme this inhibitor is of potential therapeutic value in lung diseases with elastase and proteinase 3 mediated tissue destruction.

Synthesis of Human Leukocyte Elastase Inhibitor

The polypeptide of formula I ("the prominent inhibitor") was synthesised as follows:

A DNA sequence encoding the amino-acid sequence of the polypeptide of formula I was designed according to the following considerations:

1) Single—stranded cohesive termini to allow ligation at suitable sites in a plasmid.
2) A series of restriction endonuclease sequences at the 5'-end to facilitate subsequent genetic manipulation.
3) Translation termination codons.
4) Codons at the 5'-end of the coding region were normally chosen to be A/T rich. Other codons were normally chosen as those preferred for expression in yeast and/or E.coli.

The gene was assembled from the 6 oligonucleotides shown in Table 3.

TABLE 3

| CODE | SEQUENCE (5' to 3') | Size (bases) |
|---|---|---|
| ELI1 | AAT TCG AGC TCG GTA CCA TAC CTG CAT ATG CTC AAG AAC CAG TTA AAG GTC CTG TGT CTA CTA A | 64 |
| ELI2 | CCT GGC TTA GTA GAC ACA GGA CCT TTA ACT GGT TCT TGA GCA TAT GCA GGT ATG GTA CCG AGC TCG | 66 |
| ELI3 | GCC AGG TTC TTG TCC TAT TAT CTT GAT TCG TTG CGC TAT GTT AAA CCC ACC TAA CCG TTG TTT GAA GG | 68 |
| ELI4 | TCA GTG TCC TTC AAA CAA CGG TTA GGT GGG TTT AAC ATA GCG CAA CGA ATC AAG ATA ATA GGA CAA GAA | 69 |
| ELI5 | ACA CTG ATT GTC CAG GTA TCA AAA AGT GCT GTG AAG GTT CCT GCG GTA TGG CTT GTT TCG TTC CAC AAT AAT AG | 74 |
| ELI6 | GAT CCT ATT ATT GTG GAA CGA AAC AAG CCA TAC CGC AGG AAC CTT CAC AGC ACT TTT TGA TAC CTG GAC AA | 71 |

Preparation of Oligonucleotides

The oligonucleotide sequences shown in Table 3 were prepared on an Applied Biosystems 380A DNA synthesiser from 5'-dimethoxytrityl base-protected nucleoside-2-cyanoethyl-N,N-diisopropylphosphoramidites and protected nucleosides linked to controlled-pore glass supports on a 0.2 micro mol scale, according to protocols supplied by Applied Biosystems Inc.

Each oligonucleotide, after cleavage from the solid support and removal of all protecting groups, was dissolved in water (1 ml). solution of 3M sodium acetate (pH5.6; 40 µl) and ethanol (1 ml) was added to the oligonucleotide solutions (400 µl) and the mixtures stored at −70° C. for 20 hours. The resulting precipitates were collected by centrifigation (13,000 rpm for 10 min) and the pellets washed with ethanol:water (7:3) (200 µl) then dried briefly in vacuo and dissolved in water (15 µl) and 10 µl of a formamide/dye mix. (10 mM NaOH, 0.5 mM EDTA, 0.01% Bromophenol Blue, 0.01% xylene cyanol, 80% formamide).

The oligonucleotides were purified on a 10% polyacrylamide gel in 50 mM Tris-borate (pH8.3) containing 8.3M urea. Oligonucleotides of correct length were identified by UV shadowing (Narang et al, 1979 in Methods in Enzymology Vol 68, 90–98)—normally the most prominent band—excised from the gel and electroeluted in 5 mM tris-borate (pH 8.3) at 300 mV for 3–4 hours. The aqueous solution was concentrated to about 200 μl by treatment with n-butanol (mix, spin and removal of the upper organic layer). The purified oligonucleotide was precipitated at −70° C. for 20 hours from a 0.3M sodium acetate solution by addition of ethanol (2.5 volumes).

Assembly of Gene

Oligonucleotides ELI2 to ELI5 (200 pM of each) were phosphorylated with T4 polynucleotide kinase (3.6 units) for 2 hours at 37° C. in 25 μl of a solution containing ATP (800 pM containing 25 pM gamma-$^{32}$P ATP), 100 μM spermidine, 20 mM DTT, 10 mM MgCl$_2$, 50 mM Tris-HCl (pH9.0) and 0.1 mM EDTA. The solutions were heated at 100° C. for 5 minutes to terminate the reactions, then mixed in pairs, as shown in Table 2 to give duplexes I to III. (Oligonucleotides ELI1 and ELI6 (200 mM in 25 μl) were used unphosphorylated). 0.3M Sodium acetate (pH5.6, 200 μl) and ethanol (850 μl) were added and the duplexes precipitated at −20° C. for 20 hours. The resulting precipitates were collected by centrifugation and washed with ethanol:water (7:3) then dissolved in water (50 μl). The pairs of oligonucleotides were annealed together by first heating the solutions to 100° C. for 2 min in a boiling water bath. The bath was then allowed to cool slowly to 40° C. (about 4 hours). Solutions containing duplexes I and II were combined, lyophilised and dissolved in 30 μl of a solution containing T4 DNA ligase (1 unit; BRL), 50 mM Tris (pH7.6), 10 mM magnesium chloride, 5% (w/v) PEG 8000, 1 mM ATP, 1 mm DTT. (BRL, Focus Vol 8 no 1 Winter 1986) and the DNA ligated at 30° C. for 5 minutes followed by 20 hours at 16° C. 3M Sodium acetate (20 μl) and water (150 μl) was added and the product precipitated by addition of ethanol (750 μl and cooling to −20° C. for 20 hours. The precipitate was collected by centrifugation and washed with ethanol (1 ml) then dissolved in water (15 μl) and formamide/dye mix (10 μl) and purified on a 10% polyacrylamide gel in 50 mM Tris-borate (pH8.3), 1 mM EDTA and 8.3M urea. Bands for strands of length 132 bases and 135 bases were identified by autoradiography and isolated together by electroelution from a single gel slice as described above for individual oligonucleotide sequences. The DNA strands were annealed by first heating an aqueous solution (50 μl) at 100° C. for 2 minutes, then allowing it to cool to 40° C. over 4 hours.

Duplex III was joined to the product from the above ligation (I and II), essentially as described for the preparation of that product, except that the mixture was heated to 40° C. prior to annealing the cohesive ends. The product, the gene sequence shown in FIG. 13 was purified on a 8% polyacrylamide gel and isolated as described above by electroelution from a gel slice. After precipitation, the gene was phosphorylated with T4 polynucleotide kinase as described previously for individual oligonucleotides, then dissolved in water (20 μl).

TABLE 4

| DUPLEX | OLIGO-NUCLEOTIDES | NUMBER OF BASES IN | |
|---|---|---|---|
| | | TOP STRAND | BOTTOM STRAND |
| I | ELI1 + ELI2 | 64 | 66 |
| II | ELI3 + ELI4 | 68 | 69 |
| III | ELI5 + ELI6 | 74 | 71 |

Cloning of the Synthetic Gene of Human Elastase Inhibitor

The synthetic gene described above, was cloned into the plasmid vector, pUC18 (exBRL 520-5363SA) which contains a multi-cloning sequence.

For vector preparation, 10 μg of pUC18 was dissolved in water (42 μl) and 10×B restriction buffer (BCL). The restriction endonuclease BamHI (3 μl) (BCL, 8 units/μl) was added and the mixture incubated at 37° C. for 1 hour until linearised plasmid was predominant over supercoiled and nicked circular forms. The DNA was precipitated with ethanol at 4° C. for 30 minutes, washed with ethanol:water (7:3) then dissolved in water (44 μl), 10×high salt buffer (BCL). The restriction endonuclease EcoRI (1 μl) (BCL, 90 units/μl) was added and the mixture incubated at 37° C. for 1 hour until the large EcoRI - Bam HI fragment was predominant. The DNA was precipitated at −20° C. for 20 hours, washed with ethanol:water (7:3) then dissolved in water (20 μl).

The large EcoRI - Bam HI fragment was purified on a 1% preparative agarose gel and electroeluted and precipitated as described previously, then dissolved in water (20 μl). For ligation of the synthetic gene, a mixture of vector DNA (2 μl of the EcoRI - BamHI fragment solution), synthetic gene (5 μl of the aqueous solution described previously, 5×ligase buffer (6 μl-250 mM Tris pH7.6 50 mM MgCl$_2$, 25% W/V PEG8000, 5 mM ATP, 5 mM DTT exBRL) water (15 μl) and T4 DNA ligase (2 μl unit/1 μl) was incubated at 16° C. for 4 hours. The DNA mix was used directly (either 1 μl of neat ligation mix or 2 μl of ligation mix diluted 5× with water) to transform E. coli strain HB101. The DNA mixture (1 or 2 μl) was added to competent E. coli HB101 cells (20 μl, BRL) on ice and the mixture incubated on ice for 45 min then heat shocked at 42° C. for 45 seconds. After 2 min on ice, 100 μl of SOC buffer (Bactotryptone 2%; Yeast Extract 0.5%; NaCl 10 mM; KCl 2.5 mM; MgCl$_2$, MgSO$_4$ 20 mM (10 mM each); Glucose 20 mM) was added and the mixture incubated at 37° C. for 1 hour. Aliquots of suspensions were plated onto L plates with 50 μl/ml ampicillin. Transformants were screened for the presence of cloned synthetic gene by colony hybridisation analysis using standard methods described in "Molecular Cloning; A Laboratory Manual" by Maniatis et al (Cold Spring Harbor) and in UK Patent Application No 8502605. A total of 160 colonies were streaked onto filters (Schleicher & Schuell), grown at 37° C. for 20 hours, lysed and baked. The filter was hybridised at 65° C. for 20 hours with a radioactive probe prepared from oligonucleotide sequence ELI 3 (Table 1) by use of a random-label kit (Pharmacia). Six colonies (34, 40, 42, 106, 109 and 156) giving a positive hybridisation signal were grown up in L broth at 37° C. for 20 hours on a small scale (100 ml) and plasmid DNA prepared by centrifugation in a Caesium chloride gradient essentially as described in "Molecular Cloning; A Laboratory Manual" by Maniatis et al (Cold Spring Harbor).

The DNA was sequenced by the standard chain-termination method as described by Sanger et al in Proc. Nat. Acad Sci. USA 74, 5463–5467 (1977) using a Sequenase (Trade Mark) kit (United States Biochemical Corporation). Oligonucleotides ELS1 and ELS2 (Table 5) were used as sequencing primers.

TABLE 5

| Code | (Sequence 5'–3') | Priming site (FIG. 1) |
|---|---|---|
| ELS 1 | AGCTCGGTACCATACCTGCATATGC | 7–32 (top strand) |
| ELS 2 | CTTCACAGCACTTTTTGATACCTGG | 144–168 (bottom stand) |

The plasmid DNA from clone 156 contained the sequence shown in FIG. 13 and the plasmid was designated the code pAG76. Plasmid pAG76 was used to transform competent cells of the following *E. coli* strains by standard procedures:
HB101
MSD462 (W3110 Delta lac)
MSD522 (CGSC 6300)
DH5 Alpha Expression of a Beta-galactosidase-Human Elastase Inhibitor Fusion Protein The synthetic gene sequence of the human elastase inhibitor was cloned into a commercially available vector, pUEX2 (Amersham International Plc—also deposited under the Budapest Treaty). The vector contains a gene for Beta-galactosidase under the transcriptional control of the $P_R$ promoter from bacteriophage lambda. The plasmid also contains a Beta-lactamase gene, which renders transformants containing the plasmid resistant to ampicillin, and a gene for the temperature sensitive repressor (CI857) of the $P_R$ promoter The gene was isolated from pAG76 (prepared from MSD522) following sequential digestion with EcoRI and SalI and purification of the resulting 222 bp fragment by electrophoresis on a 1% agarose gel.

The DNA fragment was isolated from the gel by first electroeluting the DNA onto DEAE NA45 paper then eluting the DNA from the NA45 paper with 1M NaCl solution. The procedure is briefly as follows:

A small piece of NA45 paper, cut to the width of the DNA band and depth of the gel, is wetted with 1×TE buffer (10 mM Tris HCl, 1 mM EDTA; pH8.0). The wetted NA45 paper is placed in a slot in the gel, cut just in front of the band to be eluted. Electrophoresis is continued for 5 min, until the DNA band is absorbed into the NA45 paper. The paper containing the DNA is first washed in 1×TE buffer then treated twice with 1M NaCL (200 μl) at 70° C. for 10 min with occasional vortexing. The NaCl solutions were combined and the DNA precipitated with ethanol (1 ml) at 4° C. for 10 min. The DNA was collected by centrifugation, washed with ethanol:water (7:3), dried and dissolvd in water (20 μl).

For vector preparation, 5 μg of pUEX2 was digested with EcoRI and SalI in high salt buffer (BCL; 50 μl) for 1 hour at 37° C. The DNA was ethanol precipitated and purified on a 1% agarose gel. The 6.7 kb vector fragment was isolated by electroelution onto NA45 paper as described above, precipitated and dissolved in water (20 μl).

For ligation, 5 μl of vector DNA (1 μg) was added to the elastase inhibitor gene fragment (10 μl, 1 μg), 5×ligase buffer (BRL; 6 μl), water (8 μl) and T4 DNA ligase (1 μl, 1 u/μl). Ligation was for 20 hours a 16° C. The DNA mix was used either directly or after 5×dilution with water to transform *E.coli* MSD462 and MSD522 cells as described previously for cloning the synthetic gene. A total of 8 colonies were obtained in MSD462 and 75 in MSD522. Six of the MSD462 colonies and 3 of the MSD522 colonies were examined by hybridisation analysis as described previously. All proved positive and were further analysed by growing up on a small scale to examine proteins expressed at 37° C. and 42° C. These small scale grows were conducted as follows:

Cultures were grown in 75 ml of M9 medium contianing 0.02% casein hydrolysate; glucose (2.0 g/l), $MgSO_4.7H_2O$ (1 mM), $CaCl_2 2H_2O$ (0.1 mM), ampicillin (50 μl/ml) and thiamine (4 μg/ml) for 20 hours at 37° C. in a shaking incubator (250 rpm). Cells were transferred to fresh medium (75 ml) to give an OD550 of 0.1 and incubated at 37° C. until the OD550 reached 0.4–0.5 then at 42° C. for 3 hours. Cells were collected by centrifugation and an aliquot lysed by boiling (100° C., 15 min) in laemmli buffer (0.125 mM Tris-HCl, pH6.8), SDS (2% w/v), glycerol (20% w/v) bromophenol blue (trace) containing freshly added Beta-mercaptoethanol (2% w/v). Proteins were examined by electrophoresis in a 20% polyacrylamide gel and staining with Coomassie Brilliant Blue. All three clones from MSD522 and five clones from MSD462 produced a new protein of higher molecular weight than a marker of Beta-galactosidase and the Beta-galactosidase protein produced by the parent pUEX2 vector. One clone from MSD522 was designated pAG77.

Preparation of Beta-galactosidase-Human Elastase Inhibitor Fusion Protein

A recombinant strain of *E. coli* MSD522 expressing the Beta-galactosidase-elastase inhibitor fusion protein (pAG77) was recovered from stock, streaked onto an L agar plate supplemented with ampicillin (50 μg/ml) and incubated at 37° C. for 20 hours. A loop of cells was transferred from this plate to each of 4×250 ml Erlenmeyer flasks containing 75 ml of M9 media supplemented as described above. These flasks were incubated by shaking at 300 rpm on an orbital incubator at 37° C. for 20 hours then at 42° C. for 4 hours.

Purification of Beta-galactosidase-Human Elastase Fusion Protein

The *E. Coli* cells were harvested and suspended in lysis buffer (15% sucrose, 50 mM EDTA, 50 mM Tris hydrochloride, pH 8.0) and lysed by treatment with lysozme/LDS (0.5 mg/ml and 0.05% respectiely) followed by sonication (4×45 seconds using an MSE Sonicator) at 4° C.

The resulting suspension was centrifuged and the pellet fraction resuspended in water followed by centrifugation.

The washed pellet was solubilised in 6M guanidine hydrochloride in phosphate buffered saline containing 50 mM beta mercaptoethanol.

This solution was dialysed extensively against phosphate buffered saline and the resulting precipitate collected by centrifugation.

The precipitate was dissolved in SDS polyacrylamide gel loading buffer and subjected to polyacrylamide gel electrophoresis using a 10% reducing gel system.

The gel was stained with Coomassie blue and the protein band corresponding to the fusion protein was cut out. This was then used as an immugen for raising antisera in rabbits.

Preparation of Elastase Inhibitor in Yeast

Yeast Secretion Vector pDP258

Figure 18:
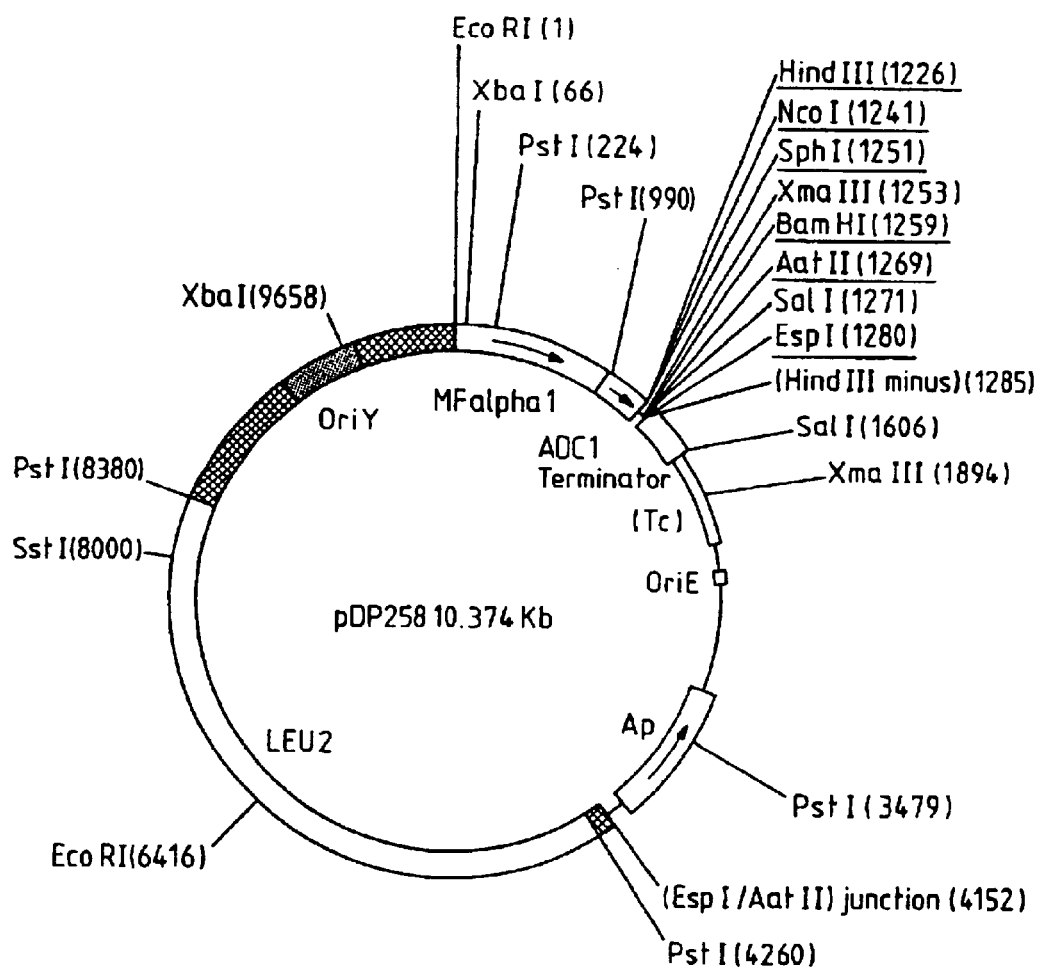
FIG. 18 illustrates the plasmid pDP258 used in the procedure for obtaining expression of mature polypeptide of formula I in yeast.

The yeast secretion vector is shown in FIG. 18 and has been deposited under the Budapest Treaty. This vector enables fusion of coding sequence to the STE13 processing signal in the MF alpha 1 prepro region. There are a number of reports describing how fusion of protein coding sequences to the STE13 signal can lead to secretion of the encoded protein, although secretion or intracellular accumulation of partially processed or unprocessed fusion proteins has also been reported. This problem can be avoided by utilising other processing sites in the MF alpha 1 prepro region. See, for example, Bitter,G. A. et al P.N.A.S. 81, 5330–5334 (1984); Brake,A. J. et al P.N.A.S. 81, 4642–4646 (1984); Zsebo, K. M. et al J. Biol. Chem. 261, 5858–5865 (1986); Loison, G. et al Bio/Technology, 6, 72–77 (1988); Ernst, J. F. DNA 7, 355–360 (1988).

The construction of pDP258, illustrated in FIG. 18 is outlined below. The position of restriction enzyme sites is approximate.

The MF alpha 1 promoter and prepro coding sequence EcoRI - HindIII fragment from the EcoRI site at −959 in Flessel, M. C et al (Genetics 121, 223–236, 1989) to the HindIII site at 263 in Kurjan, J. J & Herskowitz (cell 30, 933–943, 1982). This fragment can be derived from plasmid p69A described in Kurjan & Herskowitz (cell 30, 933–943, 1982).

The SalI(1606)-EspI/AatII region was derived from the 2550 bp SalI-AatII fragment of pBR328 (Covarrubias, L. et al. Gene 13, 25–35. 1981).

The Esp-EcoR1(1) region containing the LEU2 gene was derived from the YEp13S(YEp213) (Broach, J. R. Methods in Enzymol. 101, 307–325. 1983 and Sherman, F et al Methods in Yeast Genetics, Cold Spring Harbor 1986, p95). The HindIII site present in the 2 u sequence was destroyed by HindIII cutting, filling with Klenow polymerase and religation.

A HindIII-SphI fragment containing the ADC1 terminator derived from plasmid pAAH5 (Ammerer, G. Methods in Enzymol. 101, 192–201) was treated with T4 polymerase to create flush-ended DNA. The SalI site (shown at 1606 in FIG. 18.) was cut and filled using T4 polymerase. The ADC1 fragment was ligated with the plasmid fragment to generate a recombinant containing the ADC1 terminator in the correct orientation to terminate transcripts originating from the MF alpha 1 promoter. This cloning also regenerated the SalI site (shown) and the HindIII site (bracketed).

The polylinker containing the sites shown on the map was cloned into the HindIII site regenerated by the ADC1 terminator cloning. This polylinker was designed so that only one HindIII site was preserved by the cloning. pDP258 contains the polylinker in the orientation shown in FIG. 18. The HindIII site shown in brackets is destroyed by the polylinker cloning.

Modification of Yeast Secretion Vector

The plasmid shown in FIG. 18 was further modified to introduce restriction sites, SphI at the signal peptidase and StuI at the KEX2 processing sites in the MF alpha 1 PrePro region to enable fusion of protein coding DNA sequences to these processing signals, in order to facilitate secretion of the encoded protein to the extracellular medium. In vitro mutagenesis was performed as detailed by Amersham International plc in their "Oligonucleotide-directed in vitro mutagenesis system version 2" (code RPN.1523). Other procedures utilised in this work are known to those skilled in the art and are described, for example, in "Molecular Cloning—A Laboratory Manual" 2nd Edition. Sambrook, J. Fritsch, E. F. & T. Maniatis. C.S.H. 1989

Introduction of SphI Site at Signal Peptidase Processing Site

In order to enable fusion of the elastase inhibitor coding sequence to the MF alpha 1 "pre" secretory leader, an SphI restriction enzyme site was designed, so that following restriction and T4 polymerase treatment a blunt end is produced which terminates at the third base of the last codon (amino acid 19) of the MF alpha 1 signal sequence (see for example Ernst, J. F. DNA 7, 355–360; 1988). A mutagenic oligonucleotide primer was designed and synthesised to introduce the necessary sequence changes in the MF alpha 1 signal sequence.

```
                    FIG. 1A.
         Primer complementary to this region

*
    - --- --G CAT GC- --- --    New sequence
             | || |
    - --- --T GCT C-- --- --    Original
       ala leu ala
        17  18  19             Amino acid
                               residue
                               (Kurjan &
                               Herskowitz. 1982)
```

SphI site underlined
* = see text
| identifies bases changed using mutagenesis

The small SstI to HindIII fragment from pDP258 (see FIG. 18) was cloned into SstI+HindIII-cut RF M13mp18 DNA (BRL 520-8227SA). Potentially recombinant plaques (white on X-gal+IPTG) were characterised by small-scale preparation of RF DNA for sizing and restriction enzyme analysis by agarose gel electrophoresis. A large scale single-stranded template DNA preparation was generated from a clone containing this fragment for use in in vitro mutagenesis experiments using an oligonucleotide primer as shown in FIG. 1A). Following transformation of the mutagenised population, 15 plaques were picked and single-stranded template DNA was prepared. Following sizing by agarose gel electrophoresis, 11 templates were examined by standard chain-termination sequencing, for the appearance of an an extra T residue (complementary to the "A" asterisked in FIG. 1A). Clone #6 was then chosen from further sequencing studies which showed that there were no additional changes detected in the known MF alpha 1 promoter or coding sequence. 1 ul of a 1/100 dilution of the template DNA preparation of clone #6 was then transformed into competent TG1. Plaques were picked and inoculated into 1 ml cultures of 2×TY, previously seeded with TG1 cells (as described in the Amersham kit). These cultures were grown with shaking at 37 C for 5 hr, and used to inoculate 100 ml 2×TY media. After a further 5 hr shaking incubation double-stranded RF DNA was prepared by standard plasmid preparation methods. The small SstI–HindIII fragment from clone #6 (preparation A) was then generated by restriction enzyme cutting, and the fragment purified following separation by agarose gel electrophoresis. The purified fragment was cloned into the large HindIII–SstI pDP258 fragment (see FIG. 18) to generate pDP294 i.e. pDP258 containing an SphI site at the putative signal peptidase cleavage site (the "SIG-PEP" vector).

Introduction of StuI Site at KEX2 Processing Site

In order to enable fusion of the elastase inhibitor coding sequence to the KEX2 processing signal a StuI site was introduced by PCR mutagenesis.

```
                        FIG. 2A.
              Primer complementary to this region StuI           HindIII
-- --- --- --- AGG CCT --- -AA GCT T-- -  New sequence
                | |||
-- --- --- --- --A GAG --- --- --- --- -  Original sequence
ser leu asp lys arg
 81  82  83  84  85                       Amino acid residue
                                          (Kurjan & Herskowitz
                                          1982)
```

| identifies bases changed using PCR mutagenesis to Introduce StuI site (underlined).

Two PCR primers were generated. The first (33mer) was homologous to the MF alpha 1 sequence (Kurjan, J. & Herskowitz, I. Cell 30, 933–943. 1982) apart from the bases shown in FIG. 2A above. This primer was designed to include the new StuI site and the existing HindIII site in the PCR product. The second 30mer oligonucleotide primer was homologous to the MF alpha 1 region -211 to -241 (Flessel et al. Genetics 121:223–236. 1989) including the NsiI restriction site at -227. Using these two oligos as primers and a plasmid (e.g.pDP258) template in a PCR amplification reaction a fragment of approximately 490 bp can be generated. Following extraction with 1 volume of phenol:chloroform:isoamyl alcohol (25:24:1) and ethanol precipitation the PCR DNA product was taken up in 1 volume of water. The DNA was cut with NsiI and HindIII restriction enzymes. The product of this reaction was run on an agarose gel and the band running at 490 bp (approx) was purified by standard techniques.

A pUC18 (BRL520-5363SA) recombinant was generated containing the XbaI to HindIII region of pDP258. The NsiI site (-227 of Flessel et al) was unique in this plasmid. The NsiI-HindIII fragment in this plasmid was replaced with the PCR-generated fragment containing the new StuI site, by standard cloning techniques. Six clones were identified which contained a StuI site. Clone #6 was characterised by dideoxy sequencing as containing the new StuI site at the correct position and with no additional mutations compared to published sequences. This plasmid was designated pDP273.

The large XbaI - HindIII fragment of pDP258 and the "StuI" XbaI - HindIII fragment from pDP273 were then prepared by restriction enzyme cutting and separation on agarose gels. Following purification from the agarose gel, these fragments were ligated and transformed into competent E.coli (HB101). Small scale DNA preparations were generated from 36 colonies. The DNA was digested with StuI and SstI restriction enzymes. Clone #9 was identified as having the correct restriction enzyme pattern as visualised by agarose gel electrophoresis (pDP274). pDP274 DNA was then cut with XbaI and ligated with a purified preparation of the small XbaI fragment from pDP258. Small scale DNA preparations were made from 36 E.coli colonies transformed with this ligation mixture. Following digestion with EcoRI+ StuI two clones were identified which contained the small XbaI fragment in the correct original native orientation. One clone was prepared (pDP289) for further work. i.e. pDP258 with StuI site at the KEX2 processing site.

Cloning of Elastase Inhibitor Gene Downstream of Yeast Secretion Signals pAG76 was cut with the restriction enzyme BspMI, (see FIG. 13), then treated with T4 polymerase to fill in the 5' overhang to generate flush-ended DNA. Following extraction with phenol:chloroform:isoamylalcohol and ethanol precipitation the DNA was dissolved in water and digested with BamHI restriction enzyme. The small fragment encoding the elastase inhibitor was isolated by purification from an agarose gel. Each of the 3 vectors was then digested as described below and the large fragments isolated from agarose gels.

pDP258—cut with HindIII, treated with T4 polymerase to fill the 5' overhang, cut with BamHI.

pDP289—cut with StuI and BamHI pDP294—cut with SphI, treated with T4 polymerase to remove the 3' overhang, cut with BamHI.

Each of the three purified vector fragments was ligated with the elastase inhibitor fragment. Samples of each of the ligation mixtures were transformed into competent HB101 E.coli. 20–40 small scale DNA samples were prepared from colonies obtained with each of the three ligation mixtures. Recombinants were identified by digestion with restriction enzymes BamHI - PstI and separation of fragments on agarose gels. Clones having the correct sequence at the fusion between the MF alpha 1 signal and the elastase inhibitor coding sequence, were confirmed by DNA sequencing Clones chosen for further analysis were as follows:

pDP280 STE13/elastase inhibitor fusion i.e. derived from pDP258 pDP298 SIGPEP/elastase inhibitor fusion derived from pDP294 pDP299 KEX2/elastase inhibitor fusion derived from pDP289

These constructs were transformed (Sherman et al into JRY188 (Brake et al. P.N.A.S. 81, 4642–4646, 1984). Clones were inoculated and grown at 30° C. to stationary phase in liquid YPAD (Sherman et al, Methods in Yeast Genetics, Cold Spring Harbor 1986, p164, 165) or -LEU "drop-out" media (Synthetic Complete Medium minus leucine in Sherman et al Methods in Yeast Genetics, Cold Spring Harbor, p164, 165, 1986). Active elastase inhibitor could be detected in supernates of cultures from the pDP280 clones (see FIG. 19). Yields of material from pDP298 and pDP299 clones were lover.

The constructs were also transformed into yeast strain XS95-6C (Yeast Genetic Stock Center, University of California, Berkely, Calif. 94720). After 72 hr shaking incubation (250 rpm) at 30° C. when the culture had reached stationary phase (typically 0D600=4–6), culture supernates were harvested by pelleting whole cells. Using the enzyme assay described in below, activity was detected in culture supernates. Based on standard curves using native elastase inhibitor (see below) pDP298 clones were secreting up to 3.5 ug/ml of active elastase inhibitor into the culture supernate.

Purification of Recombinant Human Elastase Inhibitor Protein

Material obtained using the STE13 processing site (p DP280) and a host of JRY188 grown in liquid-LEU "drop-out" media was purified as follows.

The culture supernates (up to 2 liters grown in shake flasks) were filtered using a 0.22 µ filter. The filtrate was concentrated approximately ten folds using a 3000 Mr cut off filter in an Amicon spiral concentrator. The concentrate was then dialysed against 3×20 volumes of 10 mM ammonium formate (pH 4). The dialysed material was loaded onto a pre-equilibrated Sulphopropyl Sepharose column and eluted with a 10 mM to 50 mM ammonium formate gradient. Active fractions were pooled, concentrated and loaded onto a size exclusion column (Pharmacia HR100) and eluted with a phosphate buffered saline solution.

A microheterogeneous product was obtained, which on N-terminal sequencing gave mature polypeptide of formula I (60%) and mature polypeptide of formula I plus either one or two glu-ala amino acid terminal extensions. These extensions were thought to be due to incomplete processing by the yeast strain and the polypeptide with these terminal extensions were separated from the mature polypeptide of formula I by MonoS HPLC in 50 mM sodium acetate pH 4.5 using an eluent comprising a 0 to 0.5M sodium chloride gradient. The microheterogeneous product was found to have the same specific activity as that exihibited by the the polypeptide isolated from psoriatic plaques.

A similar procedure was employed to purify protein produced by cultivating constructs obtained by use of the SIGPEP and KEX2 processing sites. With these constructs a homogeneous species having the correct N-terminal sequence for mature polypeptide of formula I was obtained.

The purification procedure used with constructs grown in other hosts was essentially as above. For example, the construct obtained using the signal peptidase cleavage site was grown in yeast strain XS 956C and purified according to the above protocol to give 4 mg of mature polypeptide of formula I as a single species which exhibited the same specific activity as the polypeptide isolated from psoriatic plaques.

Assay to Determine the Presence of Elastase Inhibitor

The presence and quantity of the polypeptide of formula I during, for example its production via recombinant DNA technology, was monitored using the following assay. In this assay the activity of material was determined by the inhibition of porcine pancreatic elastase (Sigma) using N-methoxysuccinyl ala-ala-pro-val-p-nitroanilide (AAPV, Sigma) as substrate.

The sample, for example the supernate from the yeast fermentation, (100 µl) was mixed with porcine elastase (10 µg/ml) in assay buffer (0.1 M Hepes/0.5M NaCl/pH 7.5 containing 1% RIA grade bovine serum albumin). The mixture was incubated for 30 minutes at room temperature, substrate (800 µl, 2.5 mM) in assay buffer added and the mixture incubated for 2 minutes at room temperature. The rate of change of absorbance at 405 nm was measured for 2 minutes and the activity calculated from a standard curve constructed using the polypeptide of formula I isolated from psoriatic plaques (the standard was used in the range 0 to 2.5 µg/ml).

Inhibitory Activity of Recominant Elastase Inhibitor Against HLE

The recombinant elastase inhibitor produced by the methods described above was tested for inhibitory activity against human leukocyte elastase using the method described above. The recombinant polypeptide was found to have inhibitory activity comparable to that of the material obtained from psoriatic skin.

Poly LC-HPLC of Crude Recombinant Elastase Inhibitor

100 µg of crude recombinant elastase inhibitor were chromatographed on a Poly LC column and revealed to human leukocyte elastase inhibiting peaks. Two major peaks (I and II) were observed. Peak I contained 23 µg protein basing on integrated absorbance at 215 nm and 19.4 µg active inhibitor (MW 7017, titrated with HLE). Peak II contained 8.4 µg protein and 6.9 µg active inhibitor. Therefore these two peaks appeared to be essentially pure inhibitors. A coelution experiment of 1 µg Peak I and 1 µg of the polypeptide of formula I obtained from human psoriatic skin showed that Peak I and the material obrained from skin are identical in this system. This was further substantiated by a coelution experiment on $RP_{18}$-HPLC also showing a single peak.

Peak I of Poly LC-HPLC was titrated against HLE for determination of $K_i$ according to the method of Green and Work. Peak I showed a $K_i$ of $8.0 \times 10^{-10}$M in comparison to the inhibitor from human skin which showed a $K_i$ of $3.3 \times 10^{-10}$M. In respect to the accuracy of the method of Green and Work the material of Peak I is seen to be of comparable activity to the polypeptide obtained from human psoriatic skin.

This crude recombinant elastase inhibitor seems to be composed of about 75% inactive protein, 5% of a HLE inhibitor which differs from the polypeptide of formula I obtained from human skin in retention time on Poly LC-HPLC (probably due to elongation or eletion at the n-terminus) and 20% of an HLE inhibitor (Peak I in Poly LC-HPLC) identical with the polypeptide obtained from human psoriatic skin in regard of retention times in TSK 2000 size exclusion-HPLC, $RP_{18}$-HPLC, Poly LC-HPLC and inhibitory activity.

cDNA Sequence of Human Leukocyte Elastase Inhibitor

The derivation of DNA sequences coding for a particular polypeptide may be carried out using standard techniques. Such techniques include screening techniques, that is hybridisation screening of recombinant cDNA libraries with mixed oligonucleotides representing possible DNA sequence combinations, and amplification techniques, such as that known as PCR (polymerase chain reaction).

Experimental protocols for the screening of cDNA libraries by both the above methods are described in "Molecular Cloning"—Sambrook, J; Fritsch, E. F and Mariatis, T; Second Edition, Cold Spring Harbor Laboratory Press 1989.

Using the above-mentioned well known techniques the cDNA sequence was determined for the "Prominent inhibitor" (ie the polypeptide of formula I). A lung cDNA lambda gtll library was used and the sequence illustrated in FIG. 14 was obtained. The sequence was believed to continue as illustrated in FIG. 15. A translation termination codon is present after the coding sequence and a poly adenylation signal is believed to be present 153 bp further 3'. Also a 250 bp intron is thought to be present at the 3' end of the gene.

In further work cDNA clones were isolated which encode the complete amino-acid sequence of the major active component (and minor components) of preparations of the elastase inhibitor from a human lung cDNA library. FIG. 16 shows the complete DNA sequence of one such clone (EI4). This sequence was also verified in other, independent cDNA clones and from DNA fragments isolated from the same cDNA library by PCR. This sequence demonstrates the presence of upstream in-frame protein coding sequence in addition to the elastase inhibitor coding region. This upstream sequence has the following features:

a) The 19 amino-acid codons immediately upstream from the elastase inhibitor protein sequence are consistent with protein sequence data derived from a minor protein fraction (peak V, component A) identified by protein sequence analysis.
b) Six copies of a repeat peptide motif (nominally Val-Lys-Gly-Gln-X-Y, where X is either Asp, Val, Glu, Pro, Ser or Lys) from residues −26 to +10 from the start of the elastase inhibitor coding sequence. The N-termini of the various minor components of elastase inhibitor preparations are not consistent with this motif being the site of secific proteolytic cleavage.
c) The N-terminus encoded by this clone is highly hydrophobic (13 out of 18 residues) which may represent part of a signal sequence or transmembrane domain.

This clone does not contain a recognisable translation initiation codon according to conventional beliefs i.e. AUG. The results of primer extension studies reveal the start of a major transcript approximately 80 bases prior to the start of the cDNA sequence identified in mRNA from cultured human keratinocytes (HEK 78). The presence of a similar message in a range of other mRNA species (including total RNA from human lung) was not demonstrated by this technique.

Northern blot analysis of pancreatic adenocarcinoma total RNA demonstrated the presence of a homologous transcript of approximately 750 bases. This is not inconsistent with the predicted size from the above cDNA sequence of primer extension data (assuming a polyadenylation length of approximately 190 bases).

Antibodies to the Elastase Inhibitor

Antibodies were raised to the polypeptide of formula I using New Zealand White rabbits. The following vaccines were used:
1. Substrate (A), which comprised the 16 N-terminal amino acid residue of the polypeptide of formula I, coupled to bovine serum albumin via maleimidobenzoyl-n-hydroxysuccinimide ester by the method of Lerner et al (Proc. Natl. Acad. Sci. USA 78:3403–3407);
2. Substrate (A) coupled to bovine thyroglobulin as in 1 above;
3. Substrate (A) mixed with methyl-bovine serum albumin; and
4. The fusion protein of Beta galactosidase and the polypeptide of formula I.

The immunisation schedule used for the peptides listed in 1, 2 and 3 above was as follows:
Day 1—250 ug of the peptide in Freund's complete adjuvant was administered subcutaneously;
Day 39—250 ug of the peptide in Freund's incomplete adjuvant was administered subcutaneously;
Day 66—250 ug of the peptide in Freund's incomplete adjuvant was administered subcutaneously;
Day 107—1 mg of the peptide was administered intravenously without adjuvant;
Day 120—bleed.

The immunisation schedule used for the fusion protein listed in 4 above was as follows:
Day 1—200 ug of the protein vaccine in Freund's complete adjuvant was administered subcutaneously;
Day 22—100 ug of the protein vaccine in Freund's incomplete adjuvant was administered subcutaneously;
Day 61—200 ug of the protein vaccine in Freund's incomplete adjuvant was administered subcutaneously;
Day 94—130 ug of the protein vaccine without adjuvant was administered intraveneously; and
Day 107—bleed.

The cross reactivity of the antisera generated was tested using SDS PAGE and Western blotting. The antiserum generated using the fusion protein (4 above) was found to cross react with the polypeptide of formula I isolated from psoriatic plaques and also with recombinant polypeptide of formula I (1 μg detected at a dilution of 1 in 2000) and $\alpha_1$-antitrypsin. The $\alpha_1$-antitrypsin cross reactivity was removed (90%) by passing (×3) the antisera through a column comprising immobilised $\alpha_1$(25 mg $\alpha_1$-antitrypsin bound to a 5 ml cyanogen bromide activated sepharose 4B column—Parmacia). The antisera generated from the peptides listed under 1, 2 and 3 were also found to cross react with recombinant polypeptide of formula I.

Various body tissues were treated with the antisera using a titer of 1:50 and a standard immunoperoxidase technique. Strong reactivity was found wirh hepatocytes in the hepatobiliary system, slight reactivity was found with muscularis mucosae in the stomach, slight reactivity was found with lamina spinosa and venous smooth muscle cells in the tonsils, and strong reactivity with the stratum corneum, stratum granulosm, stratum spinosm and stratum basale of the epidermis of skin.

Abbreviations
AAPFpNA succinyl-alanyl-prolyl-phenylalanyl-p-nitroanilide.
AAPV-AFC methoxy-succinyl-alanyl-alanyl-prolyl-valyl-trifluoromethylcoumarine.
AAPVpNA methoxy-succinyl-alanyl-prolyl-valyl-p-nitroanilide.
TGPLpNA tosyl-glycyl-prolyl-lysine-p-nitroanalide.
HLE human leukocyte elastase.
TFA trifluoroacetic acid.
DMSO dimethylsulphoxide.
PCR Polymerase chain reaction—a method for amplifying a desired DNA sequence, see for example K. Kleppe et al J. Mol. Biol (1971), 56, 341–361; and European Patent Application, publication number 0201, 184; and "Molecular Cloning—A Laboratory Manual" 2nd Edition, Sambrook J, Fritsch, E. F and T. Maniatis. CSH 1989.

Amino Acid Notation
G or Gly: Glycine
A or Ala: Alanine
S or Ser: Serine
T or Thr: Threonine
C or Cys: Cysteine
N or Asn: Asparagine
Q or Gln: Glutamine
L or Leu: Leucine
I or Ile: Isoleucine
V or Val: Valine
M or Met: Methionine
F or Phe: Phenylalanine
Y or Tyr: Tyrosine
W or Trp: Tryptophan
P or Pro: Proline
D or Asp: Aspartic Acid
E or Glu: Glutamic Acid
H or His: Histidine
K or Lys: Lysine
R or Arg: Arginine
Standard notation is used for denoting DNA sequences.
Description of FIGS. 1 to 8
FIG. 1 illustrates Cation-Exchange-Chromatography (TSK CM 3 SE-HPLC) of an acidified extract from 50 g psoriatic scales. Column fractions were collected automatically (60 drops/fraction) and monitored for protein content as 280 nm. Fractions were assayed for HLE inhibitoractivity (HLE-I). 5 µl of each fraction were assayed for inhibitory activity towards HLE mediated proteolysis of the synthetic tetrapeptide substrate methoxy-succinyl-alanyl-alanyl-prolyl-valyl-p-nitroanilide. Inhibitory active fractions (hatched area) were combined for further purification.

FIG. 2 illustrates Reversed-Phase-$C_8$-Chromatography (Nucleosil 300 $C_8$-HPLC) of elastase inhibitor containing fractions derived from cation exchange chromatography, subjected for a second rechromatography. Protein content was continuously recorded at 215 nm. Elastase inhibitor containing fractions were combined (hatched area) and subjected to Poly LC chromatography.

Figure 3:
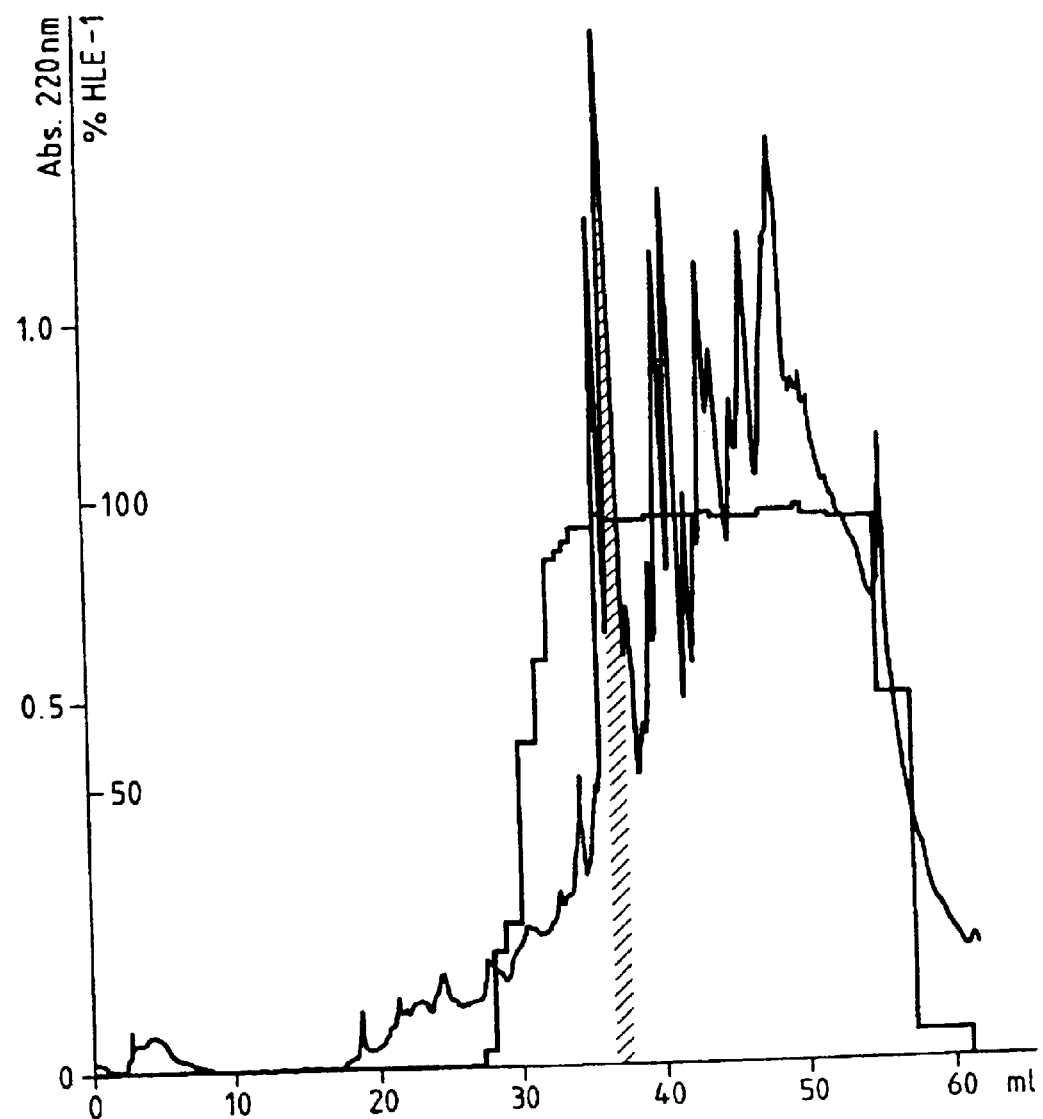
FIG. 3 illustrates a poly-sulfoethyl aspartamide chromatographic procedure used in the extraction and purification of the polypeptide of formula I from psoriatic plaques.

FIG. 3 illustrates Poly sulfoethyl aspartamide chromatography (Poly LC-HPLC) of elastase-inhibitor containing fractions derived from reversed phase $C_8$ chromatography. Protein content was recorded at 215 nm. The most prominent peak V basing on protein content and inhibitory capacity (approx. 20% of total) was collected and further purified by reversed phase $C_{18}$ chromatography.

FIG. 4 represents Reversed-Phase-$C_{18}$-Chromatography (Nucleosil 5 $C_{18}$-HPLC) of the major elastase inhibitory component derived from Poly LC-HPLC, subjected for second rechromatography. The hatched area represents the purified prominent elastase inhibitor. This preparation was used for further characterisation.

FIG. 5 apparent molecular mass of the polypeptide of formula I determined by analytical gel chromatography on TSK 2000 HPLC with 0.1% TFA as eluent. Protein content was monitored at 215 nm. As $M_r$ markers were used: Val-Gly-Ser-Glu MW 390, insulin Beta-chain fragment 22–30 MW 6512, soyabean trypsin inhibitor MW 22000. ovomucoid trypsin inhibitor MV 27000, bovine serum albumin MW 67000.

FIG. 6 isoelectric focussing of polypeptide of formula I on Servalyt$^R$ precoates pH 3–10. As standards we used Serva Test Mix 9 composed of cytochrom C (Cy-c) ribonuclease A (Rib A), myoglobulin from whale (Myo I) and myoglobulin from horse (Myo II). Gels were either stained with silver (shown on top) or sliced, eluted with acetonitril and assayed for elastase inhibitory activity (ELE-I) (shown on bottom).

FIG. 7 titration of human leukocyte elastase with the prominent elastase inhibitor (the polypeptide of formula I). Purified HLE (titrated to 1 µg/ml with recombinant eglin C) was titrated against the prominent inhibitor 0.05–0.8 µg (protein content basing on integrated absorbance at 215 nm in reversed phase $C_{18}$-HPLC). Enzyme and the prominent inhibitor were preincubated for 30 min at 21° C. and remaining activity was determined from E 1 min using 2 mM AAPV-pNA as substrate. Ki was $3 \times 10^{-10}$ M as calculated by the method of Green and Work (8).

FIG. 8 shows the sequence of the prominent elastase inhibitor, that is the polypeptide of formula I.

Details of Deposits Under the Budapest Treaty

The following plasmids have been deposited a The National Collection of Industrial and Marine Bacteria Limited, 23 St Machar Drive, Aberdeen AB2 1RY, Scotland, UK under the Budapest Treaty.

pUC18 in *E Coli* host strain CGSC 6300 (MSD 1208)
pUEX2 in *E Coli* host strain CGSC 6300 (MSD 1209)
pDP258(HB101) in *E Coli* strain HB101 (pDP258 (HB101)

References

1. Lee C T, Fein A M, Lippmann M, Holtzman H, Kimbel P, Weinbaum G. Elastolytic Activity in Pulmonary Lavage Fluid from Patients with Adult Respiratory-Distress Syndrome. (1981) New Engl J Med 304: 192–196.
2. Janoff A. Emphysema: Proteinase-Antiproteinase Imbalance. In: Gallin J I, Goldstein I, Snyderman R (eds.) Inflammation: Basic Principles and Clinical Correlates. Raven Press, N.Y., 1988.
3. Glinski W, Zarebska Z, Jablonska S, Imiela J, Norsarzewski J. The activity of polymorphonuclear leukocyte neutral proteinases and their inhibitors in patients with psoriasis treated with continuous peritoneal dialysis. (1980) J Invest Dermatol 75: 481–487.
4. Briggman R A, Schechter N M, Fraki J, Lazarus G S. Degradation of the Epidermal-Dermal Junction by Proteolytic Enzymes from Human Skin and Human Polymorphonuclear Leukocytes. (1984). J Exp Med 160: 1027–1042.
5. Fraki J E, Hopsu-Havu V K, Human Skin Proteases. Partial Purification and Characterization of a Protease Inhibitor. (1972). Arch Derm Forsch 243: 153–163.
6. Fryksmark U, Ohlsson K, Rosengren M, Tegner H. A Radioimmuno assay for Measurement and Characterisation of Human Anti-leukoprotease in Serum. (1981) Hoppe Seyler's Z Physiol Chem 362: 1273–1277.
7. Nakajima K, Powers J C, Ashe B M, Zimmerman M. Mapping the Extended Substrate Binding Site of Cathepsin G and Human Leukocyte Elastase. (1979) J Biol Chem 254: 4027–4032.
8. Green N M, Work E. Pancreatic Trypsin Inhibitor. 2. Reaction with Trypsin. (1953) Biochem J 54: 347–352.
9. Braun N J, Bodmer J L, Virca G D, Metz-Virca G, Maschler R, Bieth J G;, Schnebli H P. Kinetic Studies on the Interaction of Eglin C with Human Leukocyte Elastase and Cathepsin G. (1987) Biol Chem Hoppe-Seyler 368: 299–308.
10. Kramer M D, Justus C. The antiproteolytic compound $\alpha_2$-macro-globulin in human skin. (1988) Arch Dermatol Res 280: 93–96.
11. Fink E, Jaumann E, Fritz H, Ingrisch H, Werle E. Protease-Inhibitoren im menschlichen Spermalplasma. Isolierung durch Affinitatschromatographie und Hemmverhalten. (1971) Hoppe-Seyler's Z Physiol Chem 352: 1591–1594.
12. Wallner O, Fritz H. Characterisation of an Acid-Stable Proteinase Inhibitor in Human Cervical Mucus. (1974) Hoppe-Seyler's Z Physiol Chem 355: 709–715.
13. Ohlsson K, Tegner H, Akesson U. Isolation and Partial Characterixation of a Low Molecular Weight Acid Stable Protease Inhibitor from Human Bronchial Secretion. (1977) Hoppe-Seyler's Z Physiol Chem 358: 583–589.
14. Ohlsson M, Rosengren M, Tegner H, Ohlsson K. Quantification of Granulocyte Elastase Inhibitors in Human Mixed Saliva and in Pure Parotid Secretion. (1983) Hoppe-Seyler's Z Physiol Chem 364: 1323–1328.
15. Ohlsson K, Tegner H, Fritz H, Schiessler M. Immunological Similarity between Low Molecular Weight Trypsin-Chymotrypsin Inhibitors from Human Bronchial Secretion and Seminal Plasma. (1976) Hoppe Seyler's Z Physiol Chem 357: 1241–1244.
16. Thompson R C, Ohlsson K. Isolation, properties and complete amino acid sequence of human secretory leukocyte protease inhibitor, a potent inhibitor or leukocyte elastase. (1986) Proc Natl Acad Sci USA 83: 6692–6696.
17. Seemuller U, Arnhold M, Fritz H, Wiedenmann K, Machleidt W, Heinzel R, Appelhans H, Gassen H-G, Lottspeich F. The acid-stable proteinase inhibitor of human mucous secretions (HUSI-I, antileukoprotease). (1986).
18. Albrecht G J, Hochstrasser K, Salier J-P. Elastase Inhibition by the Inter-Alpha-Trypsin Inhibitor and 19. Fioretti E, Angeletti M, Citro G, Barra D, Ascoli F. Kunitz-type Inhibitors in Human Serum. Identification and Characterisation. (1987) J Biol Chem 262: 3586–3589.
20. Reisinger P W M, Hochstrasser K, Gottlicher I, Eulitz M, Wachter E. The Amino-Acid Sequences of the Double-Headed Proteinase Inhibitors from Cat, Lion and Dog Submandibular Glands. (1987) Biol Chem Hoppe-Seyler 368: 717–726.
21. Schalwijk J, Lammers A M, Chang A, van de Kerkhof P C M, Mier P D. An Epidermal Elastase Inhibitor Induced by Spontaneous or Experimental Inflammation. (Abstract) (1988) J Invest Dermatol 91: 376.
22. Hochstrasser K, Albrecht G J, Schonberger O L, Rasche B, Lempart K. An Elastase-Specific Inhibitor from Human Bronchial Mucus. (1981) Hoppe-Seyler's Z Physiol Chem 362: 1369–1375.

We claim:

1. An isolated nucleic acid consisting of a nucleotide sequence encoding the polypeptide: Ala-Gln-Glu-Pro-Val-Lys-GlY-Pro-Val-Ser-Thr -Lys-Pro-Gly-Ser-Cys-Pro-Ile-Ile-Leu-Ile-Arg-Cys-Ala-Met-Leu-Asn-Pro-Pro-Asn-Arg-Cys-Leu-Lys-Asp-Thr-Asp-Cys-Pro-Gly-Ile-Lys-Lys-Cys-Cys-Glu-Gly-Ser-Cys-Gly -Met-Ala-Cys-Phe-Val-Pro-Gln.

2. The nucleic acid according to claim 1 wherein said nucleotide sequence is GCTCAAGAACCAGTTAAAG-GTCCTGTGTCTACT AAGCCAGGTTCTTGTCCTAT-TATCTTGATTCGTTGCGCTATGTTAAACCCC-ACCTAACCGT TGTTTGAAGGACACTGATTGTC-CAGGTATCAAAAAGTGCTGTGAAGGTTC-CTGCGGTATG GCTTGTTTCGTTCCACAA.

3. An isolated replicable plasmid expression vehicle comprising as an insert the nucleic acid according to claim 1.

4. An isolated transformed host cell comprising the expression vehicle according to claim 3.

5. A process for the preparation of a replicable expression vehicle comprising inserting the nucleic acid according to claim 1 into a vector at an appropriate insertion site so that a replicable plasmid expression vehicle is obtained that directs the synthesis of the polypeptide encoded by said nucleic acid.

6. A process for producing a polypeptide comprising culturing the host cell according to claim 4 under conditions sufficient to produce said polypeptide.

7. A process for the preparation of a transformed host cell comprising introducing into a host cell the expression vehicle according to claim 3.

* * * * *

UNITED STATES PATENT AND TRADEMARK OFFICE
CERTIFICATE OF CORRECTION

PATENT NO. : 6,893,843 B2
DATED : May 17, 2005
INVENTOR(S) : Christophers et al.

It is certified that error appears in the above-identified patent and that said Letters Patent is hereby corrected as shown below:

Title page,
Insert Item -- [30]    Foreign Application Priority Data
Jun. 9, 1989    (GB) .............................. 8913346.6
Jun. 9, 1989    (GB) .............................. 8913349.0
Sept. 25, 1989  (GB) .............................. 8921613.9
Nov. 2, 1989    (GB) .............................. 8924717.5 --

Signed and Sealed this

Twelfth Day of July, 2005

JON W. DUDAS
*Director of the United States Patent and Trademark Office*